United States Patent
Sirdeshpande et al.

(10) Patent No.: US 10,464,872 B1
(45) Date of Patent: Nov. 5, 2019

(54) CATALYTIC GASIFICATION TO PRODUCE METHANOL

(71) Applicant: GreatPoint Energy, Inc., Chicago, IL (US)

(72) Inventors: Avinash Sirdeshpande, Chicago, IL (US); Earl Robinson, Lakeland, FL (US); Pattabhi K. Raman, Kildeer, IL (US)

(73) Assignee: GreatPoint Energy, Inc., Chicago, IL (US)

(*) Notice: Subject to any disclaimer, the term of this patent is extended or adjusted under 35 U.S.C. 154(b) by 0 days.

(21) Appl. No.: 16/050,847

(22) Filed: Jul. 31, 2018

(51) Int. Cl.
| | |
|---|---|
| *C07C 29/151* | (2006.01) |
| *C01B 3/36* | (2006.01) |
| *C01B 3/38* | (2006.01) |
| *C01B 3/58* | (2006.01) |
| *C01B 3/50* | (2006.01) |
| *C01B 3/48* | (2006.01) |
| *C01B 3/54* | (2006.01) |

(Continued)

(52) U.S. Cl.
CPC ............ *C07C 29/1518* (2013.01); *C01B 3/12* (2013.01); *C01B 3/36* (2013.01); *C01B 3/382* (2013.01); *C01B 3/48* (2013.01); *C01B 3/506* (2013.01); *C01B 3/54* (2013.01); *C01B 3/586* (2013.01); *C07C 29/153* (2013.01); *C07C 31/04* (2013.01); *C07C 43/043* (2013.01); *C10J 3/84* (2013.01); *C01B 2203/0283* (2013.01); *C01B 2203/046* (2013.01); *C01B 2203/0445* (2013.01); *C01B 2203/061* (2013.01); *C01B 2203/1041* (2013.01)

(58) Field of Classification Search
CPC ... C07C 43/043; C07C 41/34; C01B 2203/06; C01B 2203/061; C01B 2203/0244; C10J 2300/1656; C10J 2300/0976; C10J 2300/1659; C10J 2300/1655; C10J 2300/1823
See application file for complete search history.

(56) References Cited

U.S. PATENT DOCUMENTS

| | | | |
|---|---|---|---|
| 2,605,215 A | 7/1952 | Coghlan | |
| 2,694,623 A | 11/1954 | Welty, Jr. et al. | |

(Continued)

FOREIGN PATENT DOCUMENTS

| | | |
|---|---|---|
| CA | 966660 | 4/1975 |
| CA | 996353 | 9/1976 |

(Continued)

OTHER PUBLICATIONS

Asami, K., et al., "Highly Active Iron Catalysts from Ferric Chloride or the Steam Gasification of Brown Coal," ind. Eng. Chem. Res., vol. 32, No. 8, 1993, pp. 1631-1636.

(Continued)

*Primary Examiner* — Jafar F Parsa
(74) *Attorney, Agent, or Firm* — McDonnell Boehnen Hulbert & Berghoff LLP

(57) ABSTRACT

The present invention provides a process for preparing higher-value products from carbonaceous feedstocks. The process includes converting carbonaceous feedstock in a hydromethanation reactor to a methane-enriched raw product stream, converting the methane-enriched raw product stream to a methanol synthesis feed gas, then converting the methanol synthesis feed gas to higher-value products such as methanol and dimethyl ether.

13 Claims, 4 Drawing Sheets

(51) Int. Cl.
  *C10J 3/84* (2006.01)
  *C07C 31/04* (2006.01)
  *C07C 43/04* (2006.01)
  *C07C 29/153* (2006.01)
  *C01B 3/12* (2006.01)

(56) References Cited

U.S. PATENT DOCUMENTS

| | | |
|---|---|---|
| 2,791,549 A | 5/1957 | Jahnig |
| 2,809,104 A | 10/1957 | Strasser et al. |
| 2,813,126 A | 11/1957 | Tierney |
| 2,860,959 A | 11/1958 | Pettyjohn et al. |
| 2,886,405 A | 5/1959 | Benson et al. |
| 3,034,848 A | 5/1962 | King |
| 3,114,930 A | 12/1963 | Oldham et al. |
| 3,164,330 A | 1/1965 | Neidl |
| 3,351,563 A | 11/1967 | Negra et al. |
| 3,435,590 A | 4/1969 | Smith |
| 3,531,917 A | 10/1970 | Grunewald et al. |
| 3,544,291 A | 12/1970 | Schlinger et al. |
| 3,594,985 A | 7/1971 | Ameen et al. |
| 3,615,300 A | 10/1971 | Holm et al. |
| 3,689,240 A | 9/1972 | Aldridge et al. |
| 3,740,193 A | 6/1973 | Aldridge et al. |
| 3,746,522 A | 7/1973 | Donath |
| 3,759,036 A | 9/1973 | White |
| 3,779,725 A | 12/1973 | Hegarty et al. |
| 3,814,725 A | 6/1974 | Zimmerman et al. |
| 3,817,725 A | 6/1974 | Sieg et al. |
| 3,828,474 A | 8/1974 | Quartulli |
| 3,833,327 A | 9/1974 | Pitzer et al. |
| 3,840,354 A | 10/1974 | Donath |
| 3,847,567 A | 11/1974 | Kalina et al. |
| 3,876,393 A | 4/1975 | Kasai et al. |
| 3,904,386 A | 9/1975 | Graboski et al. |
| 3,915,670 A | 10/1975 | Lacey et al. |
| 3,920,229 A | 11/1975 | Piggott |
| 3,929,431 A | 12/1975 | Koh et al. |
| 3,958,957 A | 5/1976 | Koh et al. |
| 3,966,875 A | 6/1976 | Bratzler et al. |
| 3,969,089 A | 7/1976 | Moss et al. |
| 3,971,639 A | 7/1976 | Matthews |
| 3,972,693 A | 8/1976 | Wiesner et al. |
| 3,975,168 A | 8/1976 | Gorbaty |
| 3,985,519 A | 10/1976 | Kalina et al. |
| 3,989,811 A | 11/1976 | Hill |
| 3,993,457 A | 11/1976 | Cahn et al. |
| 3,996,014 A | 12/1976 | Muller et al. |
| 3,998,607 A | 12/1976 | Wesswlhoft et al. |
| 3,999,607 A | 12/1976 | Pennington et al. |
| 4,005,994 A | 2/1977 | Feldmann |
| 4,005,996 A | 2/1977 | Hausberger et al. |
| 4,011,066 A | 3/1977 | Bratzler et al. |
| 4,017,272 A | 4/1977 | Anwer et al. |
| 4,021,370 A | 5/1977 | Harris et al. |
| 4,025,423 A | 5/1977 | Stonner et al. |
| 4,044,098 A | 8/1977 | Miller et al. |
| 4,046,523 A | 9/1977 | Kalina et al. |
| 4,052,176 A | 10/1977 | Child et al. |
| 4,053,554 A | 10/1977 | Reed et al. |
| 4,057,512 A | 11/1977 | Vadovic et al. |
| 4,069,304 A | 1/1978 | Starkovish et al. |
| 4,077,778 A | 3/1978 | Nahas et al. |
| 4,091,073 A | 5/1978 | Winkler |
| 4,092,125 A | 5/1978 | Stambaugh et al. |
| 4,094,650 A | 6/1978 | Koh et al. |
| 4,100,256 A | 7/1978 | Bozzelli et al. |
| 4,101,449 A | 7/1978 | Noda et al. |
| 4,104,201 A | 8/1978 | Banks et al. |
| 4,113,615 A | 9/1978 | Gorbaty |
| 4,116,996 A | 9/1978 | Huang |
| 4,118,204 A | 10/1978 | Eakman et al. |
| 4,152,119 A | 5/1979 | Schulz |
| 4,157,246 A | 6/1979 | Eakman et al. |
| 4,159,195 A | 6/1979 | Clavenna |
| 4,162,902 A | 7/1979 | Wiesner et al. |
| 4,173,465 A | 11/1979 | Meissner et al. |
| 4,189,307 A | 2/1980 | Marion |
| 4,192,652 A | 3/1980 | Smith |
| 4,193,771 A | 3/1980 | Sharp et al. |
| 4,193,772 A | 3/1980 | Sharp |
| 4,200,439 A | 4/1980 | Lang |
| 4,204,843 A | 5/1980 | Neavel |
| 4,211,538 A | 7/1980 | Eakman et al. |
| 4,211,669 A | 7/1980 | Eakman et al. |
| 4,219,338 A | 8/1980 | Wolfs et al. |
| 4,225,457 A | 9/1980 | Schulz |
| 4,235,044 A | 11/1980 | Cheung |
| 4,243,639 A | 1/1981 | Haas et al. |
| 4,249,471 A | 2/1981 | Gunnerman |
| 4,252,771 A | 2/1981 | Lagana et al. |
| 4,260,421 A | 4/1981 | Brown et al. |
| 4,265,868 A | 5/1981 | Kamody |
| 4,270,937 A | 6/1981 | Adler et al. |
| 4,272,255 A | 6/1981 | Coates |
| 4,280,817 A | 7/1981 | Chauhan et al. |
| 4,284,416 A | 8/1981 | Nahas |
| 4,292,048 A | 9/1981 | Wesselhoft et al. |
| 4,298,584 A | 11/1981 | Makrides |
| 4,315,753 A | 2/1982 | Bruckenstein et al. |
| 4,315,758 A | 2/1982 | Patel et al. |
| 4,318,712 A | 3/1982 | Lang et al. |
| 4,318,732 A | 3/1982 | Sawyer, Jr. |
| 4,322,222 A | 3/1982 | Sass |
| 4,330,305 A | 5/1982 | Kuessner et al. |
| 4,331,451 A | 5/1982 | Isogaya et al. |
| 4,334,893 A | 6/1982 | Lang |
| 4,336,034 A | 6/1982 | Lang et al. |
| 4,336,233 A | 6/1982 | Appl et al. |
| 4,344,486 A | 8/1982 | Parrish |
| 4,347,063 A | 8/1982 | Sherwood et al. |
| 4,348,486 A | 9/1982 | Calvin et al. |
| 4,348,487 A | 9/1982 | Calvin et al. |
| 4,353,713 A | 10/1982 | Cheng |
| 4,365,975 A | 12/1982 | Williams et al. |
| 4,372,755 A | 2/1983 | Tolman et al. |
| 4,375,362 A | 3/1983 | Moss |
| 4,385,905 A | 5/1983 | Tucker |
| 4,397,656 A | 8/1983 | Ketkar |
| 4,400,182 A | 8/1983 | Davies et al. |
| 4,407,206 A | 10/1983 | Bartok et al. |
| 4,412,840 A | 11/1983 | Goksel |
| 4,425,139 A | 1/1984 | Schmidt et al. |
| 4,428,535 A | 1/1984 | Venetucci |
| 4,432,773 A | 2/1984 | Euker, Jr. et al. |
| 4,433,065 A | 2/1984 | Van Der Burgt et al. |
| 4,436,028 A | 3/1984 | Wilder |
| 4,436,531 A | 3/1984 | Estabrook et al. |
| 4,439,210 A | 3/1984 | Lancet |
| 4,443,415 A | 4/1984 | Queneau et al. |
| 4,444,568 A | 4/1984 | Beisswenger et al. |
| 4,459,138 A | 7/1984 | Soung |
| 4,462,814 A | 7/1984 | Holmes et al. |
| 4,466,828 A | 8/1984 | Tannai et al. |
| 4,468,231 A | 8/1984 | Bartok et al. |
| 4,475,924 A | 10/1984 | Meyer |
| 4,478,425 A | 10/1984 | Benko |
| 4,478,725 A | 10/1984 | Veiling et al. |
| 4,482,529 A | 11/1984 | Chen et al. |
| 4,491,609 A | 1/1985 | Degel et al. |
| 4,497,784 A | 2/1985 | Diaz |
| 4,500,323 A | 2/1985 | Siegfried et al. |
| 4,505,881 A | 3/1985 | Diaz |
| 4,514,912 A | 3/1985 | Janusch et al. |
| 4,508,544 A | 4/1985 | Moss |
| 4,508,693 A | 4/1985 | Diaz |
| 4,515,604 A | 5/1985 | Eisenlohr et al. |
| 4,515,764 A | 5/1985 | Diaz |
| 4,524,050 A | 6/1985 | Chen et al. |
| 4,540,681 A | 9/1985 | Kustes et al. |
| 4,541,841 A | 9/1985 | Reinhardt |
| 4,551,155 A | 11/1985 | Wood et al. |
| 4,558,027 A | 12/1985 | McKee et al. |
| 4,572,826 A | 2/1986 | Moore |

(56) References Cited

U.S. PATENT DOCUMENTS

| | | |
|---|---|---|
| 4,594,140 A | 6/1986 | Cheng |
| 4,597,775 A | 7/1986 | Billimoria et al. |
| 4,597,776 A | 7/1986 | Ullman et al. |
| 4,604,105 A | 8/1986 | Aquino et al. |
| 4,609,388 A | 9/1986 | Adler et al. |
| 4,609,456 A | 9/1986 | Deschamps et al. |
| 4,617,027 A | 10/1986 | Lang |
| 4,619,864 A | 10/1986 | Hendrix et al. |
| 4,620,421 A | 11/1986 | Brown et al. |
| 4,661,237 A | 4/1987 | Kimura et al. |
| 4,668,428 A | 5/1987 | Najjar |
| 4,668,429 A | 5/1987 | Najjar |
| 4,675,035 A | 6/1987 | Apffel |
| 4,678,480 A | 7/1987 | Heinrich et al. |
| 4,682,986 A | 7/1987 | Lee et al. |
| 4,690,814 A | 9/1987 | Velenyi et al. |
| 4,699,632 A | 10/1987 | Babu et al. |
| 4,704,136 A | 11/1987 | Weston et al. |
| 4,720,289 A | 1/1988 | Vaugh et al. |
| 4,747,938 A | 5/1988 | Khan |
| H478 H | 6/1988 | Blytas |
| 4,781,731 A | 11/1988 | Schlinger |
| 4,790,251 A | 12/1988 | Vidt |
| 4,803,061 A | 2/1989 | Najjar et al. |
| 4,808,194 A | 2/1989 | Najjar et al. |
| 4,810,475 A | 3/1989 | Chu et al. |
| 4,822,935 A | 4/1989 | Scott |
| 4,848,983 A | 7/1989 | Tomita et al. |
| 4,852,996 A | 8/1989 | Knop et al. |
| 4,854,944 A | 8/1989 | Strong |
| 4,861,346 A | 8/1989 | Najjar et al. |
| 4,861,360 A | 8/1989 | Apffel |
| 4,872,886 A | 10/1989 | Henley et al. |
| 4,876,080 A | 10/1989 | Paulson |
| 4,892,567 A | 1/1990 | Yan |
| 4,960,450 A | 10/1990 | Schwarz et al. |
| 4,995,193 A | 2/1991 | Soga et al. |
| 4,999,030 A | 3/1991 | Skinner et al. |
| 5,017,282 A | 5/1991 | Delbianco et al. |
| 5,055,181 A | 10/1991 | Maa et al. |
| 5,057,294 A | 10/1991 | Sheth et al. |
| 5,059,406 A | 10/1991 | Sheth et al. |
| 5,093,094 A | 3/1992 | Van Kleeck et al. |
| 5,094,737 A | 3/1992 | Bearden, Jr. et al. |
| 5,132,007 A | 7/1992 | Meyer et al. |
| 5,223,173 A | 6/1993 | Jeffrey |
| 5,225,044 A | 7/1993 | Breu |
| 5,236,557 A | 8/1993 | Muller et al. |
| 5,242,470 A | 9/1993 | Salter et al. |
| 5,250,083 A | 10/1993 | Wolfenbarger et al. |
| 5,277,884 A | 1/1994 | Shinnar et al. |
| 5,354,345 A | 10/1994 | Nehls, Jr. |
| 5,435,940 A | 7/1995 | Doering et al. |
| 5,485,728 A | 1/1996 | Dickinson |
| 5,500,044 A | 3/1996 | Meade et al. |
| 5,505,746 A | 4/1996 | Chriswell et al. |
| 5,536,893 A | 7/1996 | Gudmundsson |
| 5,616,154 A | 4/1997 | Elliott et al. |
| 5,630,854 A | 5/1997 | Sealock, Jr. et al. |
| 5,635,147 A | 6/1997 | Herbert et al. |
| 5,641,327 A | 6/1997 | Leas |
| 5,660,807 A | 8/1997 | Forg et al. |
| 5,669,960 A | 9/1997 | Couche |
| 5,670,122 A | 9/1997 | Zamansky et al. |
| 5,720,785 A | 2/1998 | Baker |
| 5,733,515 A | 3/1998 | Doughty et al. |
| 5,769,165 A | 6/1998 | Bross et al. |
| 5,776,212 A | 7/1998 | Leas |
| 5,785,721 A | 7/1998 | Brooker |
| 5,788,724 A | 8/1998 | Carugati et al. |
| 5,865,898 A | 2/1999 | Holtzapple et al. |
| 5,855,631 A | 6/1999 | Leas |
| 5,968,465 A | 10/1999 | Koveal et al. |
| 6,013,158 A | 1/2000 | Wootten |
| 6,015,104 A | 1/2000 | Rich, Jr. |
| 6,028,234 A | 2/2000 | Heinemann et al. |
| 6,090,356 A | 7/2000 | Jahnke et al. |
| 6,132,478 A | 10/2000 | Tsurui et al. |
| 6,180,843 B1 | 1/2001 | Heinemann et al. |
| 6,187,465 B1 | 2/2001 | Galloway |
| 6,379,645 B1 | 4/2002 | Bucci et al. |
| 6,389,820 B1 | 5/2002 | Rogers et al. |
| 6,419,888 B1 | 7/2002 | Wyckoff |
| 6,506,349 B1 | 1/2003 | Khanmamedov |
| 6,506,361 B1 | 1/2003 | Machado et al. |
| 6,602,326 B2 | 8/2003 | Lee et al. |
| 6,641,625 B1 | 11/2003 | Clawson et al. |
| 6,653,516 B1 | 11/2003 | Yoshikawa et al. |
| 6,692,711 B1 | 2/2004 | Alexion et al. |
| 6,790,430 B1 | 9/2004 | Lackner et al. |
| 6,797,253 B2 | 9/2004 | Lyon |
| 6,808,543 B2 | 10/2004 | Paisley |
| 6,830,597 B1 | 12/2004 | Green |
| 6,841,279 B1 | 1/2005 | Foger et al. |
| 6,855,852 B1 | 2/2005 | Jackson et al. |
| 6,878,358 B2 | 4/2005 | Vosteen et al. |
| 6,894,183 B2 | 5/2005 | Choudhary et al. |
| 6,955,595 B2 | 10/2005 | Kim |
| 6,955,695 B2 | 10/2005 | Nahas |
| 6,969,494 B2 | 11/2005 | Herbst |
| 7,056,359 B1 | 6/2006 | Somerville et al. |
| 7,074,373 B1 | 7/2006 | Warren et al. |
| 7,118,720 B1 | 10/2006 | Mendelsohn et al. |
| 7,132,183 B2 | 11/2006 | Galloway |
| 7,168,488 B2 | 1/2007 | Olsvik et al. |
| 7,205,448 B2 | 4/2007 | Gajda et al. |
| 7,220,502 B2 | 5/2007 | Galloway |
| 7,309,383 B2 | 12/2007 | Beech, Jr. et al. |
| 7,481,275 B2 | 1/2009 | Olsvik et al. |
| 7,666,383 B2 | 2/2010 | Green |
| 7,758,663 B2 | 7/2010 | Rabovitser et al. |
| 7,897,126 B2 | 3/2011 | Rappas et al. |
| 7,901,644 B2 | 3/2011 | Rappas et al. |
| 7,922,782 B2 | 4/2011 | Sheth |
| 7,926,750 B2 | 4/2011 | Hauserman |
| 7,976,593 B2 | 7/2011 | Graham |
| 8,021,445 B2 | 9/2011 | Shaffer |
| 8,114,176 B2 | 2/2012 | Nahas |
| 8,114,177 B2 | 2/2012 | Hippo et al. |
| 8,123,827 B2 | 2/2012 | Robinson |
| 8,163,048 B2 | 4/2012 | Rappas et al. |
| 8,192,716 B2 | 6/2012 | Raman et al. |
| 8,202,913 B2 | 6/2012 | Robinson et al. |
| 8,268,899 B2 | 9/2012 | Robinson et al. |
| 8,286,901 B2 | 10/2012 | Rappas et al. |
| 8,297,542 B2 | 10/2012 | Rappas et al. |
| 8,328,890 B2 | 12/2012 | Reiling et al. |
| 8,349,039 B2 | 1/2013 | Robinson |
| 8,361,428 B2 | 1/2013 | Raman et al. |
| 8,366,795 B2 | 2/2013 | Raman et al. |
| 8,479,833 B2 | 7/2013 | Raman |
| 8,479,834 B2 | 7/2013 | Preston |
| 8,502,007 B2 | 8/2013 | Hippo et al. |
| 8,557,878 B2 | 10/2013 | Rappas et al. |
| 8,647,402 B2 | 2/2014 | Robinson et al. |
| 8,648,121 B2 | 2/2014 | Rappas et al. |
| 8,652,222 B2 | 2/2014 | Raman et al. |
| 8,652,696 B2 | 2/2014 | Sirdeshpande |
| 8,653,149 B2 | 2/2014 | Robinson et al. |
| 8,669,013 B2 | 3/2014 | Powell et al. |
| 8,709,113 B2 | 4/2014 | Raman et al. |
| 8,728,182 B2 | 5/2014 | Sirdeshpande et al. |
| 8,728,183 B2 | 5/2014 | Reiling et al. |
| 8,733,459 B2 | 5/2014 | Wallace |
| 8,734,547 B2 | 5/2014 | Rappas et al. |
| 8,734,548 B2 | 5/2014 | Rappas et al. |
| 8,748,687 B2 | 6/2014 | Sirdeshpande |
| 8,999,020 B2 | 4/2015 | Raman et al. |
| 9,012,524 B2 | 4/2015 | Robinson et al. |
| 9,034,058 B2 | 5/2015 | Robinson et al. |
| 9,034,061 B2 | 5/2015 | Robinson et al. |
| 9,127,221 B2 | 9/2015 | Sirdeshpande |
| 9,234,149 B2 | 1/2016 | Lau et al. |
| 9,273,260 B2 | 3/2016 | Robinson et al. |

(56) References Cited

U.S. PATENT DOCUMENTS

| | | |
|---|---|---|
| 9,328,920 B2 | 5/2016 | Sirdeshpande et al. |
| 9,353,322 B2 | 5/2016 | Raman et al. |
| 2002/0036086 A1 | 3/2002 | Minkkinen et al. |
| 2003/0009943 A1 | 1/2003 | Millet et al. |
| 2003/0070808 A1 | 4/2003 | Allison |
| 2003/0131582 A1 | 7/2003 | Anderson |
| 2003/0167691 A1 | 9/2003 | Nahas |
| 2004/0020123 A1 | 2/2004 | Kimura et al. |
| 2004/0023086 A1 | 2/2004 | Su et al. |
| 2004/0055716 A1 | 3/2004 | Landalv et al. |
| 2004/0123601 A1 | 7/2004 | Fan |
| 2004/0180971 A1 | 9/2004 | Inoue et al. |
| 2004/0256116 A1 | 12/2004 | Olsvik et al. |
| 2005/0107648 A1 | 5/2005 | Kimura et al. |
| 2005/0137442 A1 | 6/2005 | Gajda et al. |
| 2005/0192362 A1 | 9/2005 | Rodriguez et al. |
| 2005/0274113 A1 | 12/2005 | Sekiai et al. |
| 2005/0287056 A1 | 12/2005 | Baker et al. |
| 2005/0288537 A1 | 12/2005 | Maund et al. |
| 2006/0120953 A1 | 6/2006 | Okuyama et al. |
| 2006/0149423 A1 | 7/2006 | Barnicki et al. |
| 2006/0228290 A1 | 10/2006 | Green |
| 2006/0233687 A1 | 10/2006 | Hojlund Nielsen |
| 2006/0265953 A1 | 11/2006 | Hobbs |
| 2007/0000177 A1 | 1/2007 | Hippo et al. |
| 2007/0051043 A1 | 3/2007 | Schingnitz |
| 2007/0083072 A1 | 4/2007 | Nahas |
| 2007/0149423 A1 | 6/2007 | Warr et al. |
| 2007/0180990 A1 | 8/2007 | Downs et al. |
| 2007/0186472 A1 | 8/2007 | Rabovister et al. |
| 2007/0220810 A1 | 9/2007 | Leveson et al. |
| 2007/0227729 A1 | 10/2007 | Zubrin et al. |
| 2007/0237696 A1 | 10/2007 | Payton |
| 2007/0277437 A1 | 12/2007 | Sheth |
| 2007/0282018 A1 | 12/2007 | Jenkins |
| 2008/0022586 A1 | 1/2008 | Gilbert et al. |
| 2008/0027150 A1* | 1/2008 | Steynberg ............... C07C 1/20 518/700 |
| 2008/0072495 A1 | 3/2008 | Waycuilis |
| 2008/0134888 A1 | 6/2008 | Chao et al. |
| 2008/0141591 A1 | 6/2008 | Kohl |
| 2008/0223046 A1 | 9/2008 | Yakobson et al. |
| 2009/0012188 A1 | 1/2009 | Rojey et al. |
| 2009/0048476 A1 | 2/2009 | Rappas et al. |
| 2009/0090055 A1 | 4/2009 | Ohtsuka |
| 2009/0090056 A1 | 4/2009 | Ohtsuka |
| 2009/0139851 A1 | 6/2009 | Freel |
| 2009/0165361 A1 | 7/2009 | Rappas et al. |
| 2009/0165376 A1 | 7/2009 | Lau et al. |
| 2009/0165379 A1 | 7/2009 | Rappas |
| 2009/0165380 A1 | 7/2009 | Lau et al. |
| 2009/0165381 A1 | 7/2009 | Robinson |
| 2009/0165382 A1 | 7/2009 | Rappas et al. |
| 2009/0165383 A1 | 7/2009 | Rappas et al. |
| 2009/0165384 A1 | 7/2009 | Lau et al. |
| 2009/0166588 A1 | 7/2009 | Spitz et al. |
| 2009/0169448 A1 | 7/2009 | Rappas et al. |
| 2009/0169449 A1 | 7/2009 | Rappas et al. |
| 2009/0170968 A1 | 7/2009 | Nahas et al. |
| 2009/0173079 A1 | 7/2009 | Wallace et al. |
| 2009/0217575 A1 | 9/2009 | Raman et al. |
| 2009/0217582 A1 | 9/2009 | May et al. |
| 2009/0217584 A1 | 9/2009 | Raman et al. |
| 2009/0217585 A1 | 9/2009 | Raman et al. |
| 2009/0217586 A1 | 9/2009 | Rappas et al. |
| 2009/0217587 A1 | 9/2009 | Raman et al. |
| 2009/0217588 A1 | 9/2009 | Hippo et al. |
| 2009/0217589 A1 | 9/2009 | Robinson |
| 2009/0217590 A1 | 9/2009 | Rappas et al. |
| 2009/0218424 A1 | 9/2009 | Hauserman |
| 2009/0220406 A1 | 9/2009 | Rahman |
| 2009/0229182 A1 | 9/2009 | Raman et al. |
| 2009/0235585 A1 | 9/2009 | Neels et al. |
| 2009/0236093 A1 | 9/2009 | Zubrin et al. |
| 2009/0246120 A1 | 10/2009 | Raman et al. |
| 2009/0259080 A1 | 10/2009 | Raman et al. |
| 2009/0260287 A1 | 10/2009 | Lau |
| 2009/0305093 A1 | 12/2009 | Biollaz et al. |
| 2009/0324458 A1 | 12/2009 | Robinson et al. |
| 2009/0324459 A1 | 12/2009 | Robinson et al. |
| 2009/0324460 A1 | 12/2009 | Robinson et al. |
| 2009/0324461 A1 | 12/2009 | Robinson et al. |
| 2009/0324462 A1 | 12/2009 | Robinson et al. |
| 2010/0005710 A1 | 1/2010 | Shaffer |
| 2010/0011658 A1 | 1/2010 | Bruso |
| 2010/0071235 A1 | 3/2010 | Pan et al. |
| 2010/0071262 A1 | 3/2010 | Robinson et al. |
| 2010/0074829 A1 | 3/2010 | Koss |
| 2010/0076235 A1 | 3/2010 | Reiling et al. |
| 2010/0120926 A1 | 5/2010 | Robinson et al. |
| 2010/0121125 A1 | 5/2010 | Hippo et al. |
| 2010/0159352 A1 | 6/2010 | Gelin et al. |
| 2010/0168494 A1 | 7/2010 | Rappas et al. |
| 2010/0168495 A1 | 7/2010 | Rappas et al. |
| 2010/0179232 A1 | 7/2010 | Robinson et al. |
| 2010/0270506 A1 | 10/2010 | Goetsch et al. |
| 2010/0287835 A1 | 11/2010 | Reiling et al. |
| 2010/0287836 A1 | 11/2010 | Robinson et al. |
| 2010/0292350 A1 | 11/2010 | Robinson et al. |
| 2011/0031439 A1 | 2/2011 | Sirdeshpande et al. |
| 2011/0062012 A1 | 3/2011 | Robinson |
| 2011/0062721 A1 | 3/2011 | Sirdeshpande et al. |
| 2011/0062722 A1 | 3/2011 | Sirdeshpande et al. |
| 2011/0064648 A1 | 3/2011 | Preston et al. |
| 2011/0088896 A1 | 4/2011 | Preston |
| 2011/0088897 A1 | 4/2011 | Raman |
| 2011/0089271 A1 | 4/2011 | Werner |
| 2011/0146978 A1 | 6/2011 | Perlman |
| 2011/0146979 A1 | 6/2011 | Wallace |
| 2011/0197501 A1 | 8/2011 | Taulbee |
| 2011/0207002 A1 | 8/2011 | Powell et al. |
| 2011/0217602 A1 | 9/2011 | Sirdeshpande |
| 2011/0262323 A1 | 10/2011 | Rappas et al. |
| 2012/0046510 A1 | 2/2012 | Sirdeshpande |
| 2012/0060417 A1 | 3/2012 | Raman et al. |
| 2012/0102836 A1 | 5/2012 | Raman et al. |
| 2012/0102837 A1 | 5/2012 | Raman et al. |
| 2012/0210635 A1 | 8/2012 | Edwards |
| 2012/0213680 A1 | 8/2012 | Rappas et al. |
| 2012/0271072 A1 | 10/2012 | Robinson et al. |
| 2012/0305848 A1 | 12/2012 | Sirdeshpande |
| 2013/0042824 A1 | 2/2013 | Sirdeshpande |
| 2013/0046124 A1 | 2/2013 | Sirdeshpande |
| 2013/0172640 A1 | 7/2013 | Robinson et al. |
| 2014/0090584 A1 | 4/2014 | Sirdeshpande et al. |
| 2014/0094636 A1 | 4/2014 | Robinson et al. |
| 2015/0166910 A1 | 6/2015 | Robinson et al. |
| 2015/0299588 A1 | 10/2015 | Spitz et al. |

FOREIGN PATENT DOCUMENTS

| | | |
|---|---|---|
| CA | 1003217 | 1/1977 |
| CA | 1041553 | 10/1978 |
| CA | 1106178 | 8/1981 |
| CA | 1 125 026 | 6/1982 |
| CA | 1187702 | 6/1985 |
| CA | 1282243 | 4/1991 |
| CA | 1299589 | 4/1992 |
| CA | 1332108 | 9/1994 |
| CA | 2 673 121 A1 | 6/2008 |
| CA | 2713642 | 7/2009 |
| CN | 1477090 | 2/2004 |
| CN | 1554569 A | 12/2004 |
| CN | 101028925 A | 9/2007 |
| CN | 101074397 A | 11/2007 |
| CN | 101555420 | 10/2009 |
| CN | 101745435 | 6/2010 |
| DE | 2 210 891 | 3/1972 |
| DE | 2210891 | 9/1972 |
| DE | 2852710 | 6/1980 |
| DE | 3422202 | 12/1985 |
| DE | 100610607 | 6/2002 |
| EA | 819 | 4/2000 |
| EP | 0024792 | 3/1981 |

(56) References Cited

FOREIGN PATENT DOCUMENTS

| | | |
|---|---|---|
| EP | 0007247 B1 | 11/1982 |
| EP | 0 067 580 | 12/1982 |
| EP | 102828 | 3/1984 |
| EP | 0 138 463 | 4/1985 |
| EP | 0 225 146 | 6/1987 |
| EP | 0 259 927 | 3/1988 |
| EP | 0473153 | 3/1992 |
| EP | 0 723 930 | 7/1996 |
| EP | 1 001 002 | 5/2000 |
| EP | 1 004 746 A1 | 5/2000 |
| EP | 1 136 542 A1 | 9/2001 |
| EP | 1 207 132 | 5/2002 |
| EP | 1 741 673 | 6/2006 |
| EP | 1768207 | 3/2007 |
| EP | 2058471 | 5/2009 |
| FR | 797 089 | 4/1936 |
| FR | 2 478 615 | 9/1981 |
| FR | 2906879 | 4/2008 |
| GB | 593910 | 10/1947 |
| GB | 640907 | 8/1950 |
| GB | 676615 | 7/1952 |
| GB | 701 131 | 12/1953 |
| GB | 760627 | 11/1956 |
| GB | 798741 | 7/1958 |
| GB | 820 257 | 9/1959 |
| GB | 996327 | 6/1965 |
| GB | 1033764 | 6/1966 |
| GB | 1328053 | 8/1973 |
| GB | 1448562 | 9/1976 |
| GB | 1453081 | 10/1976 |
| GB | 1467219 | 3/1977 |
| GB | 1467995 | 3/1977 |
| GB | 1 599 932 | 7/1977 |
| GB | 1554948 | 10/1979 |
| GB | 1560873 | 2/1980 |
| GB | 1595612 | 8/1981 |
| GB | 1595622 | 8/1981 |
| GB | 2078251 | 1/1982 |
| GB | 2154600 | 9/1985 |
| GB | 2455864 | 6/2009 |
| JP | S28-6633 | 12/1953 |
| JP | S35-11945 | 8/1960 |
| JP | 53-94305 | 8/1978 |
| JP | 53-111302 | 9/1978 |
| JP | 54020003 | 2/1979 |
| JP | 54-150402 | 11/1979 |
| JP | 55-12181 | 1/1980 |
| JP | 56-145982 | 11/1981 |
| JP | 56157493 | 12/1981 |
| JP | S58-27312 B2 | 6/1983 |
| JP | 60-35092 | 2/1985 |
| JP | 60-77938 | 5/1985 |
| JP | S61-44995 A | 3/1986 |
| JP | 62241991 | 10/1987 |
| JP | 62 257985 | 11/1987 |
| JP | 03115491 | 5/1991 |
| JP | 2000290659 | 10/2000 |
| JP | 2000290670 | 10/2000 |
| JP | 2002105467 | 4/2002 |
| JP | 2004-132689 | 4/2004 |
| JP | 2004292200 | 10/2004 |
| JP | 2004298818 | 10/2004 |
| JP | 2006 169476 A | 6/2006 |
| KR | 10-1073780 | 10/2011 |
| WO | 9641070 A1 | 12/1996 |
| WO | 2000/18681 | 4/2000 |
| WO | WO 2000/043468 | 7/2000 |
| WO | WO 2002/040768 | 5/2002 |
| WO | WO 2002/079355 | 10/2002 |
| WO | 2002/103157 | 12/2002 |
| WO | 2003/018958 | 3/2003 |
| WO | WO 2003/033624 | 4/2003 |
| WO | 2004/055322 A1 | 7/2004 |
| WO | 2004/055323 | 7/2004 |
| WO | WO 2004/072210 | 8/2004 |
| WO | WO 2006/031011 | 3/2006 |
| WO | WO 2007/005284 | 1/2007 |
| WO | WO 2007/047210 | 4/2007 |
| WO | 2007/068682 | 6/2007 |
| WO | 2007/077137 | 7/2007 |
| WO | 2007/077138 | 7/2007 |
| WO | 2007/083072 | 7/2007 |
| WO | WO 2007/076363 | 7/2007 |
| WO | WO 2007/128370 | 11/2007 |
| WO | 2007/143376 | 12/2007 |
| WO | WO 2007/143376 | 12/2007 |
| WO | 2008/055591 A2 | 5/2008 |
| WO | 2008/058636 | 5/2008 |
| WO | WO 2008/073889 | 6/2008 |
| WO | 2008/087154 | 7/2008 |
| WO | 2009/018053 | 2/2009 |
| WO | WO 2009/018053 | 2/2009 |
| WO | WO 2009/048723 | 4/2009 |
| WO | WO 2009/048724 | 4/2009 |
| WO | 2009/086408 A1 | 7/2009 |
| WO | WO 2009/086361 | 7/2009 |
| WO | WO 2009/086362 | 7/2009 |
| WO | WO 2009/086363 | 7/2009 |
| WO | WO 2009/086366 | 7/2009 |
| WO | WO 2009/086367 | 7/2009 |
| WO | WO 2009/086370 | 7/2009 |
| WO | WO 2009/086372 | 7/2009 |
| WO | WO 2009/086374 | 7/2009 |
| WO | WO 2009/086377 | 7/2009 |
| WO | WO 2009/086383 | 7/2009 |
| WO | WO 2009/086407 | 7/2009 |
| WO | WO 2009/086408 | 7/2009 |
| WO | WO 2009/111330 | 9/2009 |
| WO | WO 2009/111331 | 9/2009 |
| WO | WO 2009/111332 | 9/2009 |
| WO | WO 2009/111335 | 9/2009 |
| WO | WO 2009/111342 | 9/2009 |
| WO | WO 2009/111345 | 9/2009 |
| WO | WO 2009/124017 | 10/2009 |
| WO | WO 2009/124019 | 10/2009 |
| WO | WO 2009/158576 | 12/2009 |
| WO | WO 2009/158579 | 12/2009 |
| WO | WO 2009/158580 | 12/2009 |
| WO | WO 2009/158582 | 12/2009 |
| WO | WO 2009/158583 | 12/2009 |
| WO | WO 2010/033846 | 3/2010 |
| WO | WO 2010/033848 | 3/2010 |
| WO | WO 2010/033850 | 3/2010 |
| WO | WO 2010/033852 | 3/2010 |
| WO | WO 2010/048493 | 4/2010 |
| WO | WO 2010/078297 | 7/2010 |
| WO | WO 2010/078298 | 7/2010 |
| WO | 2010/132549 A2 | 11/2010 |
| WO | WO 2010/132551 | 11/2010 |
| WO | 2011/017630 A1 | 2/2011 |
| WO | 2011/029278 | 3/2011 |
| WO | 2011/029282 | 3/2011 |
| WO | 2011/029283 | 3/2011 |
| WO | 2011/029284 | 3/2011 |
| WO | 2011/029285 | 3/2011 |
| WO | 2011/034888 A1 | 3/2011 |
| WO | 2011/034889 A1 | 3/2011 |
| WO | 2011/034891 A1 | 3/2011 |
| WO | WO 2011/034890 | 3/2011 |
| WO | 2011/049858 A2 | 4/2011 |
| WO | 2011/049861 A2 | 4/2011 |
| WO | 2011/063608 | 6/2011 |
| WO | 2011/076994 A1 | 6/2011 |
| WO | 2011/084580 A2 | 7/2011 |
| WO | 2011/084581 A1 | 7/2011 |
| WO | 2011/106285 A1 | 9/2011 |
| WO | 2011/139694 A1 | 11/2011 |
| WO | 2011/150217 A2 | 12/2011 |
| WO | WO 2012/024369 | 2/2012 |
| WO | 2012/033997 A1 | 3/2012 |
| WO | 2012/061235 A1 | 5/2012 |
| WO | 2012/061238 A1 | 5/2012 |
| WO | 2012/116003 A1 | 8/2012 |
| WO | 2012/145497 A1 | 10/2012 |

(56) References Cited

FOREIGN PATENT DOCUMENTS

| WO | 2012/166879 A1 | 12/2012 |
|---|---|---|
| WO | 2013/025808 A1 | 2/2013 |
| WO | 2013/025812 A1 | 2/2013 |
| WO | 2013/052553 A1 | 4/2013 |

OTHER PUBLICATIONS

Berger, R., et al., "High Temperature $CO_2$-Absorption: A Process Offering New Prospects in Fuel Chemistry," The Fifth International Symposium on Coal Combustion, Nov. 2003, Nanjing, China, pp. 547-549.
Brown et al., "Biomass-Derived Hydrogen From A Thermally Ballasted Gasifier," DOE Final Technical Report, Award No. DE-FC36-01GO11091, Aug. 2005, 197 pages.
Brown et al., "Biomass-Derived Hydrogen From A Thermally Ballasted Gasifier," DOE Hydrogen Program Contractors' Review Metting, Center for Sustainable Environmental Technologies, Iowa State University, May 21, 2003.
Cohen, S.J., Project Manager, "Large Pilot Plant Alternatives for Scaleup of the Catalytic Coal Gasification Process," FE-2480-20, U.S. Dept. of Energy, Contract No. EX-76-C-01-2480, 1979.
Euker, Jr., C.A., Reitz, R.A., Program Managers, "Exxon Catalytic Coal-Gasification-Process Development Program," Exxon Research & Engineering Company, FE-2777-31, U.S. Dept. of Energy, Contract No. ET-78-C-01-2777, 1981.
Kalina, T., Nahas, N.C., Project Managers, "Exxon Catalaytic Coal Gasification Process Predevelopment Program," Exxon Research & Engineering Company, FE-2369-24, U.S. Dept. of Energy, Contract No. E(49-18)-2369, 1978.
Nahas, N.C., "Exxon Catalytic Coal Gasification Process—Fundamentals to Flowsheets," Fuel, vol. 62, No. 2, 1983, pp. 239-241.
Ohtsuka, Y. et al., "Highly Active Catalysts from Inexpensive Raw Materials for Coal Gasification," Catalysis Today, vol. 39, 1997, pp. 111-125.
Ohtsuka, Yasuo et al, "Steam Gasification of Low-Rank Coals with a Chlorine-Free Iron Catalyst from Ferric Chloride," Ind. Eng. Chem. Res., vol. 30, No. 8, 1991, pp. 1921-1926.
Ohtsuka, Yasuo et al., "Calcium Catalysed Steam Gasification of Yalourn Brown Coal," Fuel, vol. 65, 1986, pp. 1653-1657.
Ohtsuka, Yasuo, et al, "Iron-Catalyzed Gasification of Brown Coal at Low Temperatures," Energy & Fuels, vol. 1, No. 1, 1987, pp. 32-36.
Ohtsuka, Yasuo, et al., "Ion-Exchanged Calcium From Calcium Carbonate and Low-Rank Coals: High Catalytic Activity in Steam Gasification," Energy & Fuels 1996, 10, pp. 431-435.
Ohtsuka, Yasuo et al., "Steam Gasification of Coals with Calcium Hydroxide," Energy & Fuels, vol. 9, No. 6, 1995, pp. 1038-1042.
Pereira, P., et al., "Catalytic Steam Gasification of Coals," Energy & Fuels, vol. 6, No. 4, 1992, pp. 407-410.
Ruan Xiang-Quan, et al., "Effects of Catalysis on Gasification of Tatong Coal Char," Fuel, vol. 66, Apr. 1987, pp. 568-571.
Tandon, D., "Low Temperature and Elevated Pressure Steam Gasification of Illinois Coal," College of Engineering in the Graduate School, Southern Illinois university at Carbondale, Jun. 1996.
A.G. Collot et al., "Co-pyrolysis and co-gasification of coal and biomass in bench-scale fixed-bed and fluidized bed reactors", (1999) Fuel 78, pp. 667-679.
Wenkui Zhu et al., "Catalytic gasification of char from co-pyrolysis of coal and biomass", (2008) Fuel Processing Technology, vol. 89, pp. 890-896.
Chiesa P. et al., "Co-Production of hydrogen, electricity and C02 from coal with commercially ready technology. Part A: Performance and emissions", (2005) International Journal of Hydrogen Energy, vol. 30, No. 7, pp. 747-767.
Brown et al., "Biomass-Derived Hydrogen From a Thermally Ballasted Gasifier", DOE Hydrogen Program Contractors' Review meeting, May 18-21, 2003, Center for Sustainable Environmental Technologies Iowa State University.
Brown et al., "Biomass-Derived Hydrogen From A thermally Ballasted Gasifier", Final Technical Report, Iowa State University, Aug. 2005.
Chiaramonte et al, "Upgrade Coke by Gasification", (1982) Hydrocarbon Processing, vol. 61 (9), pp. 255-257 (Abstract only).
Pipeline Rules of Thumb Handbook, Ed. E.W. McAllister, 2002. (Abstract only).
Classification of Coal Engineering Toolbox (to establish ash content of bituminous and anthracite coal) [Retrieved from the internet Nov. 12, 2018:<http://www.engineeringtoolbox.com/classification-coal-d_164.html>] (Dec. 21, 2007).
Fluidized Bed Gasifier—National Energy Technology Laboratory [Retrieved from the internet Nov. 12, 2018: <https://www.netl.doe.gov/research/coal/energy-systems/gasification/gasifipedia/fluidizedbed>].
Moriyama, et al., "Upgrading of Low Rank Coal as Coal Water Slurry and its Utilization", Coal Preparation, 2005, vol. 25, pp. 193-210. (Abstract only).
Organic Chemical Technology, Jinmin Dou, pp. 75-77, Chemical Industry Press, ISBN 7-5025-8071-9, 1991.
Powder River Coal Company [Retrieved from the internet Nov. 13, 2018:<URL:http://web.ccsd.k12.wy.us/mines/PR/CoalTypes.html>].
U.S. Department of Energy, National Energy Technology Laboratory Report titled "Detailed Coal Specifications" issued Jan. 2012. (Abstract only).
Gerdes, Kristin, et al., "Integrated Gasification Fuel Cell Performance and Cost Assessment," National Energy Technology Laboratory, U.S. Department of Energy, Mar. 27, 2009, pp. 1-26.
Ghosh, S., et al., "Energy Analysis of a Cogeneration Plant Using Coal Gasification and Solid Oxide Fuel Cell," Energy, 2006, vol. 31, No. 2-3, pp. 345-363.
Jeon, S.K., et al., "Characteristics of Steam Hydrogasification of Wood Using A Micro-Batch Reactor," Fuel, 2007, vol. 86, pp. 2817-2823.
Li, Mu, et al., "Design of Highly Efficient Coal-Based Integrated Gasification Fuel Cell Power Plants," Journal of Sower Sources, 2010, vol. 195, pp. 5707-5718.
Prins, M.J., et al., "Exergetic Optimisation of a Production Process of Fischer-Tropsch Fuels from Biomass," Fuel Processing Technology, 2005, vol. 86, No. 4, pp. 375-389.
U.S. Appl. No. 13/450,995, filed Apr. 19, 2012.
U.S. Appl. No. 12/778,538, filed May 12, 2010, Robinson, et al.
U.S. Appl. No. 12/778,548, filed May 12, 2010, Robinson, et al.
U.S. Appl. No. 12/778,552, filed May 12, 2010, Robinson, et al.
Adsorption, http://en.wikipedia.org/wiki/Adsorption, pp. 1-8, Oct. 2, 2007.
Amine gas treating, http://en.wikipedia.org/wiki/Acid_gas_removal, pp. 1-4, [Accessed from the Internet on Nov. 1, 2007].
Coal, http://en.wikipedia.org/wiki/Coal_gasification, pp. 1-8, Oct. 29, 2007.
Coal Data: A Reference, Energy Information Administration, Office of Coal, Nuclear, Electric, and Alternate Fuels U.S. Department of Energy, DOE/EIA-0064(93), Feb. 1995.
Deepak Tandon, Dissertation Approval, "Low Temperature and Elevated Pressure Steam Gasification of Illinois Coal", Jun. 13, 1996.
Demibras, "Demineralization of Agricultural Residues by Water Leaching", *Energy Sources*, vol. 25, pp. 679-687, (2003).
Fluidized Bed Gasifiers, http://www.energyproducts.com/fluidized_bed_gasifiers.htm, pp. 1-5, [Accessed from the Internet on Jan. 6, 2007].
Gas separation, http://en.wikipedia.org/wiki/Gas_separation, pp. 1-2, Feb. 24, 2007.
Gasification, http://en.wikipedia.org/wiki/Gasification, pp. 1-6, [Accessed from the Internet on Nov. 6, 2007].
Gallagher Jr., et al., "Catalytic Coal Gasification for SNG Manufacture", *Energy Research*, vol. 4, pp. 137-147, (1980).
Heinemann, et al., "Fundamental and Exploratory Studies of Catalytic Steam Gasification of Carbonaceous Materials", Final Report Fiscal Years 1985-1994.

(56) References Cited

OTHER PUBLICATIONS

Jensen, et al. Removal of K and Cl by leaching of straw char, *Biomass and Bioenergy*, vol. 20, pp. 447-457, (2001).

Mengjie, et al., "A potential renewable energy resource development and utilization of biomass energy", http://www.fao.org.docrep/T4470E/t4470e0n.htm, pp. 1-8, [Accessed from the Internet on Jan. 24, 2008].

Meyers, et al. Fly Ash as A Construction Material for Highways, A Manual. Federal Highway Administration, Report No. FHWA-IP-76-16, Washington, DC, 1976, pp. 1-198.

Coal Bottom Ash/Boiler Slag, http://www.p2pays.org/ref/13/12842/cbabs2.htm, pp. 1-7, [Accessed from the Internet on Aug. 7, 2018].

Natural gas processing, http://en.wikipedia.org/wiki/Natural_gas_processing, pp. 1-4, [Accessed from the Internet on Nov. 1, 2007].

Natural Gas Processing: The Crucial Link Between Natural Gas Production and Its Transportation to Market. Energy Information Administration, Office of Oil and Gas; pp. 1-11, (2006).

Prins, et al., "Exergetic optimisation of a production process of Fischer-Tropsch fuels from biomass", *Fuel Processing Technology*, vol. 86, pp. 375-389, (2004).

Reboiler, http://en.wikipedia.org/wiki/Reboiler, pp. 1-4, [Accessed from the Internet on Jan. 14, 2008].

What is XPS?, http://www.nuance.northwestern.edu/Keckll/xps1.asp, pp. 1-2, [Accessed from the Internet on Jan. 31, 2008].

2.3 Types of gasifiers, http://www.fao.org/docrep/t0512e/T0512e0a.htm, pp. 1-6, [Accessed from the Internet on Nov. 6, 2007].

2.4 Gasification fuels, http://www.fao.org/docrep/t0512e/T0512e0b.htm#TopofPage, pp. 1-8, [Accessed from the Internet on Nov. 6, 2007].

2.5 Design of downdraught gasifiers, http://www.fao.org/docrep/t0512e/T0512e0c.htm#TopOfPage, pp. 1-8, [Accessed from the Internet on Nov. 6, 2007].

2.6 Gas cleaning and cooling, http://www.fao.org/docrep/t0512e0d.htm#TopOFPage, pp. 1-3, [Accessed from the Internet on Nov. 6, 2007].

Moulton, Lyle K. "Bottom Ash and Boiler Slag", *Proceedings of the Third International Ash Utilization Symposium*, U.S. Bureau of Mines, Information Circular No. 8640, Washington, DC, 1973.

Coal Conversion Processes (Gasification); Encyclopedia of Chemical Technology, 4th Edition, vol. 6, pp. 541-566, (Jan. 1991).

* cited by examiner

CATALYTIC GASIFICATION TO PRODUCE METHANOL

FIELD OF THE INVENTION

The present invention relates generally to processes for preparing higher-value products from carbonaceous feedstocks.

BACKGROUND OF THE INVENTION

Methanol is an important industrial chemical that has many uses including (a) as a fuel or fuel additive, (b) as a raw material for production of chemicals such as formaldehyde and acetic acid, and (c) as an industrial solvent (windshield washer fluid, antifreeze, hydrate inhibitor).

Methanol is produced from a methanol synthesis gas comprised mainly of hydrogen, carbon monoxide and carbon dioxide with essentially no methane. Methanol synthesis proceeds via the following catalytic reactions:

$$CO + 2H_2 \leftrightarrow CH_3OH$$

$$CO_2 + 3H_2 \leftrightarrow CH_3OH + H_2O$$

Side reactions include the formation of dimethyl ether and higher alcohols. The production of methanol is maximized when the module number R defined below is at an optimum value in the range of 2 to 2.1:

$$R = \frac{H_2 - CO_2}{CO + CO_2}$$

The feedstock for producing synthesis gas is either natural gas or a solid hydrocarbon such as coal or petroleum coke. In some instances, heavy petroleum liquids such as asphaltenes or biomass have also been used.

The methanol synthesis gas is conventionally generated by one of the following routes: (1) steam reforming of natural gas, (2) autothermal reforming of natural gas and (3) noncatalytic gasification of solid hydrocarbonaceous feedstocks such as coal or petroleum coke with oxygen.

Each of the methods of synthesis gas generation produces synthesis gas having a natural module number that is not close to the optimum value of 2 to 2.1. Steam reforming of natural gas produces a synthesis gas with R=3 to 3.5. This results in an excess of hydrogen that must either be sold as a by-product or combusted as fuel in a fired heater. Autothermal reforming of natural gas with steam and oxygen produces a synthesis gas with R=1.7 to 1.8. This method is closest to being optimal and a viable option since considerable development in autothermal reforming technology and catalysts has taken place. Conventional noncatalytic gasification of coal and petroleum coke produces a synthesis gas with R=0.4 to 0.6. The high operating temperature (2600-2900° F.; about 1427-1593° C.) results in high oxygen consumption and a low R value of less than 1. The large deficiency of hydrogen must be met by subjecting a significant fraction of the synthesis gas to the water-gas shift reaction:

$$CO + H_2O \leftrightarrow H_2 + CO_2$$

Shifting the gas to increase the module number is undesirable since it lowers the carbon conversion to methanol. Thus, the natural module number of synthesis gas production technologies is either undesirable in terms of hydrogen conversion or in terms of carbon conversion.

SUMMARY OF THE INVENTION

To overcome the problem of a suboptimal module number with steam reforming of natural gas, the combined reforming route has been proposed as an optimal alternative. In this method, a portion of the natural gas is fed to a conventional reformer to produce a hydrogen-rich synthesis gas with R=3. The reformer product is then blended with the balance of the natural gas to produce a methane-rich gas that is then fed to an autothermal reformer. Here, the addition of steam and oxygen at a controlled rate allows a final product with the optimal R to be obtained by partial oxidation and reforming of methane.

Since noncatalytic gasification of coal or petroleum coke has practically no methane in the outlet gas, a combined reforming type concept is not possible.

The present invention combines catalytic gasification with an autothermal reformer (ATR) unit to produce a methanol synthesis feed gas with an optimal module number for methanol synthesis feed gas production and, ultimately, to produce products such as methanol and dimethyl ether from the methanol synthesis feed gas. This invention reduces oxygen and byproduct carbon dioxide and increases methanol yield per unit mass of solid carbonaceous feedstock in comparison to conventional oxygen blown gasification technologies. Similar advantages will accrue to other syngas-based manufacturing processes.

In contrast to the noncatalytic gasification of coal or petroleum coke, the catalytic gasification of coal or petroleum coke takes place in the presence of an alkali metal catalyst that permits operation at a low temperature (1300° F.; about 704° C.). The catalyst simultaneously enhances the rates of three reactions: steam-carbon gasification, water gas shift and methanation. Thus, a major portion of the heat required for the endothermic gasification reaction is balanced by heat generated by the exothermic shift and methanation reactions. A relatively small amount of oxygen is needed for partial oxidation of solid carbon and some of the generated syngas. Catalytic gasification enables efficient conversion of carbon contained in a solid hydrocarbon feedstock to a methane-rich synthesis gas at low temperature. Carbon is predominantly converted through steam-char gasification that generates carbon and hydrogen rather than combustion products.

The product of catalytic gasification is a methane-rich raw gas with $H_2$:CO molar ratio of at least 1.5 and a methane content of at least 25 mol % on a dry, $CO_2$-free basis. The high methane content of the product gas from catalytic gasification after cooling, dehydration and acid gas removal allows it to be processed in an autothermal reformer to produce a methanol synthesis feed gas with an optimal module number. This concept is like combined reforming of natural gas in that the catalytic gasification of coal produces a gas similar to the mixed gas entering the autothermal reformer of a combined reforming process.

The present invention relates to the catalytic gasification of hydrocarbon feedstocks to produce methanol via intermediate autothermal reforming. Unlike noncatalytic gasification where all the oxygen is fed to the gasifier to convert carbon to a suboptimal module number, the oxygen in a catalytic gasification process is split between a catalytic gasifier operating at low temperature to convert the carbon and an autothermal reformer to convert the methane-rich gasifier product to methanol synthesis feed gas.

The present invention also combines catalytic gasification with a cryogenic separation unit that will also produce a methanol synthesis feed gas with an optimal module number for methanol synthesis feed gas production and, ultimately, to produce products such as methanol and dimethyl ether from the methanol synthesis feed gas. The combination of catalytic gasification and cryogenic separation also produces a methane product that can be used directly as substitute natural gas.

The details of the hydromethanation of carbonaceous feedstocks are described next. The hydromethanation of a carbon source typically involves four reactions:

Steam carbon: $C+H_2O \rightarrow CO+H_2$     (I)

Water-gas shift: $CO+H_2O \rightarrow H_2+CO_2$     (II)

CO Methanation: $CO+3H_2 \rightarrow CH_4+H_2O$     (III)

Hydro-gasification: $2H_2+C \rightarrow CH_4$     (IV)

In the hydromethanation reaction, the first three reactions (I-III) predominate to result in the following overall net reaction:

$2C+2H_2O \rightarrow CH_4+CO_2$     (V)

The overall hydromethanation reaction is essentially thermally balanced; however, due to process heat losses and other energy requirements (such as required for evaporation of moisture entering the reactor with the feedstock), some heat must be added to maintain the thermal balance.

In one variation of the hydromethanation process, required carbon monoxide, hydrogen and heat energy can also at least in part be generated in situ by feeding oxygen into the hydromethanation reactor. See, for example, previously incorporated US2010/0076235A1, US2010/0287835A1 and US2011/0062721A1, as well as commonly-owned US2012/0046510A1, US2012/0060417A1, US2012/0102836A1, US2012/0102837A1, US2013/0046124A1, US2013/0042824A1, US2013/0172640A1 and US2014/0094636A1.

The result is a "direct" methane-enriched raw product gas stream also containing substantial amounts of hydrogen, carbon monoxide and carbon dioxide which can, for example, be directly utilized as a medium BTU energy source, or can be processed to result in a variety of higher-value product streams such as pipeline-quality substitute natural gas, high-purity hydrogen, methanol, ammonia, higher hydrocarbons, carbon dioxide (for enhanced oil recovery and industrial uses) and electrical energy.

A char by-product stream is also produced in addition to the methane-enriched raw product gas stream. The solid char by-product contains unreacted carbon, entrained hydromethanation catalyst and other inorganic components of the carbonaceous feedstock. The by-product char may contain 20 wt % or more carbon depending on the feedstock composition and hydromethanation conditions.

This by-product char is periodically or continuously removed from the hydromethanation reactor, and typically sent to a catalyst recovery and recycle operation to improve economics and commercial viability of the overall process. The nature of catalyst components associated with the char extracted from a hydromethanation reactor and methods for their recovery are disclosed, for example, in previously incorporated US2007/0277437A1, US2009/0165383A1, US2009/0165382A1, US2009/0169449A1 and US2009/0169448A1, as well as commonly-owned US2011/0262323A1 and US2012/0213680A1. Catalyst recycle can be supplemented with makeup catalyst as needed, such as disclosed in previously incorporated US2009/0165384A1.

In particular, the invention provides a process for generating a methanol synthesis feed gas from a non-gaseous carbonaceous material and a hydromethanation catalyst, the process comprising the steps of:

a. preparing a carbonaceous feedstock from the non-gaseous carbonaceous material;

b. introducing the carbonaceous feedstock, a hydromethanation catalyst, high-pressure, superheated steam, oxygen into a hydromethanation reactor;

c. reacting the carbonaceous feedstock in the hydromethanation reactor at an operating temperature from about 800° F. (about 427° C.) up to about 1500° F. (about 816° C.), and an operating pressure of at least about 250 prig (about 1825 kPa), to produce a by-product char, and a methane-enriched raw product gas comprising methane, carbon monoxide, hydrogen, carbon dioxide, hydrogen sulfide, steam, heat energy and entrained fines;

d. withdrawing a stream of the by-product char from the hydromethanation reactor as the by-product char stream, wherein the by-product char stream comprises a carbon content and entrained hydromethanation catalyst;

e. removing a substantial portion of the entrained fines from the methane-enriched raw product gas to form a fines-cleaned methane-enriched raw product gas;

f. cooling the fines-cleaned methane-enriched raw product gas to generate steam and a cooled stream;

g. removing additional particulates from the cooled stream to generate a particle-depleted cooled gas;

h. generating a methanol synthesis feed gas by:
(i). using autothermal reforming by the steps of:
A. further cooling the particle-depleted cooled gas to generate steam, then recovering the ammonia present in the cooled effluent in an ammonia recovery system to generate an ammonia-depleted effluent;
B. removing a substantial portion of the carbon dioxide and a substantial portion of the hydrogen sulfide from the ammonia-depleted effluent in an acid gas removal unit to produce a sweetened gas, wherein the sweetened gas comprises hydrogen, carbon monoxide and methane, and has greater than 25% methane on a dry, CO2-free basis;
C. mixing the sweetened gas with high-pressure, super-heated steam and heating the mixture to produce a product stream;
D. mixing the product stream with oxygen and feeding the mixture into an autothermal reformer unit to form an effluent gas; and
E. cooling the effluent gas to generate steam and a methanol synthesis feed gas, wherein the methanol synthesis feed gas comprises hydrogen, carbon monoxide and carbon dioxide;

or (ii). using cryogenic separation and co-producing substitute natural gas by the steps of:
A. forming a hydrogen-enriched raw product gas by
I. introducing a portion of the particle-depleted cooled gas into a water-gas shift reactor and steam shifting at least a portion of the carbon monoxide to generate an effluent gas; and
II. combining the remaining portion of the particle-depleted cooled gas with the effluent gas generated by steam shifting to form hydrogen-enriched raw product gas;
with the proviso that part A is carried out only when the module number of the methanol synthesis feed gas produced in part E is less than 1.75;
B. cooling the particle-depleted cooled gas, or the hydrogen-enriched raw product gas, if present, to generate steam and a cooled effluent;

C. recovering the ammonia present in the cooled effluent in an ammonia recovery system to generate an ammonia-depleted effluent;

D. removing a substantial portion of the carbon dioxide and a substantial portion of the hydrogen sulfide from the ammonia-depleted effluent in acid gas removal unit to produce a sweetened gas; and E. feeding the sweetened gas into a cryogenic separator and separating the gas into a substitute natural gas stream and a methanol synthesis feed gas.

The methanol may be generated from the methanol synthesis feed gas.

The process has a steam demand and a power demand that are met by internal energy integration such that the process requires no net import of steam or power.

The hydromethanation catalyst may comprise an alkali metal such as potassium.

The process may further comprise treating all or a portion of the by-product char stream in a catalyst recovery unit comprising a quench tank and a quench medium, by:

a. quenching the by-product char stream with the quench medium to extract a portion of the entrained catalyst to generate a carbon- and catalyst-depleted char and liberated hydromethanation catalyst;

b. withdrawing a stream of carbon- and catalyst-depleted char from the catalyst recovery unit as the carbon- and catalyst-depleted char stream; and c. withdrawing a stream of liberated hydromethanation catalyst from the catalyst recovery unit as the recovered hydromethanation catalyst stream.

The process may also further comprise feeding at least a portion of the recovered primary fines stream, the recovered secondary fines stream, or both, to the catalyst recovery unit. Further, the hydromethanation catalyst may comprise at least a portion of the recovered hydromethanation catalyst stream.

When the methanol synthesis feed gas is generated by the autothermal reforming process, the product stream produced in step h, part (i).C, may have a temperature of at least 1000° F. (538° C.). In addition, the methanol synthesis feed gas produced in step h, part (i). E, may have a module number in the range of 1.75 to 2.

Finally, the invention also provides a process for preparing dimethyl ether from the methanol synthesis feed gas or from methanol generated from the methanol synthesis feed gas, wherein the methanol synthesis feed gas has been prepared using either autothermal reforming or cryogenic separation with the co-production of substitute natural gas.

DETAILED DESCRIPTION

Figure 1:
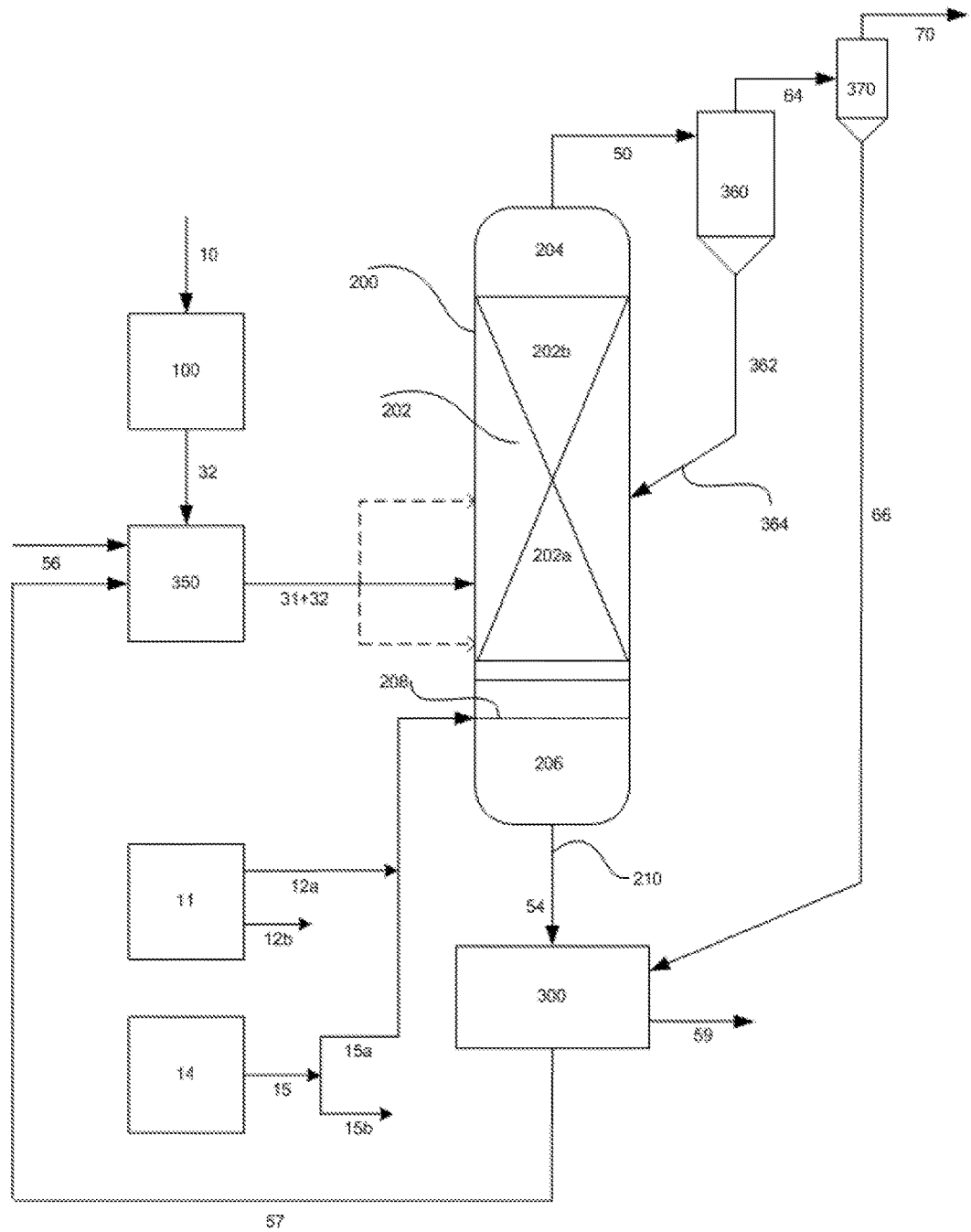
FIG. 1 is a schematic representation of the hydromethanation reactor including the hydrocarbonaceous feed system, catalyst application system, catalyst recovery and recycle system, a primary external cyclone for recirculating the entrained solids to the reactor and a secondary external cyclone for removing the fines from the methane-rich raw gas stream.

The present invention relates to processes for converting a non-gaseous carbonaceous material ultimately into a syngas with an optimal module number R for subsequent use in the manufacture of methanol, dimethyl ether, liquid fuels and other syngas derived chemicals or products. In the context of the present description, all publications, patent applications, patents and other references mentioned herein, if not otherwise indicated, are explicitly incorporated by reference herein in their entirety for all purposes as if fully set forth.

Unless otherwise defined, all technical and scientific terms used herein have the same meaning as commonly understood by one of ordinary skill in the art to which this disclosure belongs. In case of conflict, the present specification, including definitions, will control.

Except where expressly noted, trademarks are shown in upper case.

Unless stated otherwise, all percentages, parts, ratios, etc., are by weight.

Unless stated otherwise, pressures expressed in psi units are gauge, and pressures expressed in kPa units are absolute.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus.

Further, unless expressly stated to the contrary, "or" and "and/or" refers to an inclusive and not to an exclusive. For example, a condition A or B, or A and/or B, is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the disclosure. This description should be read to include one or at least one, and the singular also includes the plural unless it is obvious that it is meant otherwise.

The term "substantial", as used herein, unless otherwise defined herein, means that greater than about 90% of the referenced material, preferably greater than about 95% of the referenced material, and more preferably greater than about 97% of the referenced material. If not specified, the percent is on a molar basis when reference is made to a molecule (such as methane, carbon dioxide, carbon monoxide and hydrogen sulfide), and otherwise is on a weight basis (such as for entrained fines).

The term "predominant portion", as used herein, unless otherwise defined herein, means that greater than 50% of the referenced material. If not specified, the percent is on a molar basis when reference is made to a molecule (such as hydrogen, methane, carbon dioxide, carbon monoxide and hydrogen sulfide), and otherwise is on a weight basis (such as for entrained fines).

The term "depleted" is synonymous with reduced from originally present. For example, removing a substantial portion of a material from a stream would produce a material-depleted stream that is substantially depleted of that material. Conversely, the term "enriched" is synonymous with greater than originally present.

The term "carbonaceous" as used herein is synonymous with hydrocarbon.

The term "carbonaceous material" as used herein is a material containing organic hydrocarbon content. Carbonaceous materials can be classified as biomass or non-biomass materials as defined herein.

The term "biomass" as used herein refers to carbonaceous materials derived from recently (for example, within the past 100 years) living organisms, including plant-based biomass and animal-based biomass. For clarification, biomass does not include fossil-based carbonaceous materials, such as coal. For example, see previously incorporated US2009/0217575A1, US2009/0229182A1 and US2009/0217587A1.

The term "plant-based biomass" as used herein means materials derived from green plants, crops, algae, and trees, such as, but not limited to, sweet sorghum, bagasse, sugarcane, bamboo, hybrid poplar, hybrid willow, albizzia trees, eucalyptus, alfalfa, clover, oil palm, switchgrass, Sudan grass, millet, jatropha, and Miscanthus (e.g., *Miscanthus* x *gigantean*). Biomass further include wastes from agricultural cultivation, processing, and/or degradation such as corn cobs and husks, corn stover, straw, nut shells, vegetable oils, canola oil, rapeseed oil, biodiesels, tree bark, wood chips, sawdust, and yard wastes.

The term "animal-based biomass" as used herein means wastes generated from animal cultivation and/or utilization. For example, biomass includes, but is not limited to, wastes from livestock cultivation and processing such as animal manure, guano, poultry litter, animal fats, and municipal solid wastes (e.g., sewage).

The term "non-biomass", as used herein, means those carbonaceous materials which are not encompassed by the term "biomass" as defined herein. For example, non-biomass includes, but is not limited to, anthracite, bituminous coal, sub-bituminous coal, lignite, petroleum coke, asphaltenes, liquid petroleum residues or mixtures thereof. For example, see US2009/0166588A1, US2009/0165379A1, US2009/0165380A1, US2009/0165361A1, US2009/0217590A1 and US2009/0217586A1.

"Liquid heavy hydrocarbon materials" are viscous liquid or semi-solid materials that are flowable at ambient conditions or can be made flowable at elevated temperature conditions. These materials are typically the residue from the processing of hydrocarbon materials such as crude oil. For example, the first step in the refining of crude oil is normally a distillation to separate the complex mixture of hydrocarbons into fractions of differing volatility. A typical first-step distillation requires heating at atmospheric pressure to vaporize as much of the hydrocarbon content as possible without exceeding an actual temperature of about 650° F. (about 343° C.), since higher temperatures may lead to thermal decomposition. The fraction which is not distilled at atmospheric pressure is commonly referred to as "atmospheric petroleum residue". The fraction may be further distilled under vacuum, such that an actual temperature of up to about 650° F. (about 343° C.) can vaporize even more material. The remaining undistillable liquid is referred to as "vacuum petroleum residue". Both atmospheric petroleum residue and vacuum petroleum residue are considered liquid heavy hydrocarbon materials for the purposes of the present invention.

Non-limiting examples of liquid heavy hydrocarbon materials include vacuum resids; atmospheric resids; heavy and reduced petroleum crude oils; pitch, asphalt and bitumen (naturally occurring as well as resulting from petroleum refining processes); tar sand oil; shale oil; bottoms from catalytic cracking processes; coal liquefaction bottoms; and other hydrocarbon feed streams containing significant amounts of heavy or viscous materials such as petroleum wax fractions.

The term "asphaltene" as used herein is an aromatic carbonaceous solid at room temperature, and can be derived, for example, from the processing of crude oil and crude oil tar sands. Asphaltenes may also be considered liquid heavy hydrocarbon feedstocks.

The liquid heavy hydrocarbon materials may inherently contain minor amounts of solid carbonaceous materials, such as petroleum coke and/or solid asphaltenes, that are generally dispersed within the liquid heavy hydrocarbon matrix, and that remain solid at the elevated temperature conditions utilized as the feed conditions for the present process.

The terms "petroleum coke" and "petcoke" as used herein include both (i) the solid thermal decomposition product of high-boiling hydrocarbon fractions obtained in petroleum processing (heavy residues—"resid petcoke"); and (ii) the solid thermal decomposition product of processing tar sands (bituminous sands or oil sands—"tar sands petcoke"). Such carbonization products include, for example, green, calcined, needle and fluidized bed petcoke.

Resid petcoke can also be derived from a crude oil, for example, by coking processes used for upgrading heavy-gravity residual crude oil (such as a liquid petroleum residue), which petcoke contains ash as a minor component, typically about 1.0 wt % or less, and more typically about 0.5 wt % of less, based on the weight of the coke. Typically, the ash in such lower-ash cokes predominantly comprises metals such as nickel and vanadium.

Tar sands petcoke can be derived from an oil sand, for example, by coking processes used for upgrading oil sand. Tar sands petcoke contains ash as a minor component, typically in the range of about 2 wt % to about 12 wt %, and more typically in the range of about 4 wt % to about 12 wt %, based on the overall weight of the tar sands petcoke. Typically, the ash in such higher-ash cokes predominantly comprises materials such as silica and/or alumina.

Petroleum coke can comprise at least about 70 wt % carbon, at least about 80 wt % carbon, or at least about 90 wt % carbon, based on the total weight of the petroleum coke. Typically, the petroleum coke comprises less than about 20 wt % inorganic compounds, based on the weight of the petroleum coke.

The term "coal" as used herein means peat, lignite, sub-bituminous coal, bituminous coal, anthracite, or mixtures thereof. In certain embodiments, the coal has a carbon content of less than about 85%, or less than about 80%, or less than about 75%, or less than about 70%, or less than about 65%, or less than about 60%, or less than about 55%, or less than about 50% by weight, based on the total coal weight. In other embodiments, the coal has a carbon content ranging up to about 85%, or up to about 80%, or up to about 75% by weight, based on the total coal weight. Examples of useful coal include, but are not limited to, Illinois #6, Pittsburgh #8, Beulah (ND), Utah Blind Canyon, and Powder River Basin (PRB) coals. Anthracite, bituminous coal, sub-bituminous coal, and lignite coal may contain about 10 wt %, from about 5 to about 7 wt %, from about 4 to about 8 wt %, and from about 9 to about 11 wt %, ash by total weight of the coal on a dry basis, respectively. However, the ash content of any particular coal source will depend on the rank and source of the coal, as is familiar to those skilled in the art. See, for example, "Coal Data: A Reference", Energy Information Administration, Office of Coal, Nuclear, Electric and Alternate Fuels, U.S. Department of Energy, DOE/EIA-0064(93), February 1995.

The ash produced from combustion of a coal typically comprises both a fly ash and a bottom ash, as is familiar to those skilled in the art. The fly ash from a bituminous coal can comprise from about 20 to about 60 wt % silica and from about 5 to about 35 wt % alumina, based on the total weight of the fly ash. The fly ash from a sub-bituminous coal can comprise from about 40 to about 60 wt % silica and from about 20 to about 30 wt % alumina, based on the total weight of the fly ash. The fly ash from a lignite coal can comprise from about 15 to about 45 wt % silica and from about 20 to about 25 wt % alumina, based on the total weight of the fly ash. See, for example, Meyers, et al. "Fly Ash. A Highway Construction Material," Federal Highway Administration, Report No. FHWA-IP-76-16, Washington, D C, 1976.

The bottom ash from a bituminous coal can comprise from about 40 to about 60 wt % silica and from about 20 to about 30 wt % alumina, based on the total weight of the bottom ash. The bottom ash from a sub-bituminous coal can comprise from about 40 to about 50 wt % silica and from about 15 to about 25 wt % alumina, based on the total weight of the bottom ash. The bottom ash from a lignite coal can comprise from about 30 to about 80 wt % silica and from about 10 to about 20 wt % alumina, based on the total weight of the bottom ash. See, for example, Moulton, Lyle K. "Bottom Ash and Boiler Slag," Proceedings of the Third International Ash Utilization Symposium, U.S. Bureau of Mines, Information Circular No. 8640, Washington, D C, 1973.

A material such as methane can be biomass or non-biomass under the above definitions depending on its source of origin.

A "non-gaseous" material is substantially a liquid, semi-solid, solid or mixture at ambient conditions. For example, coal, petcoke, asphaltene and liquid petroleum residue are non-gaseous materials, while methane and natural gas are gaseous materials.

The term "unit" refers to a unit operation. When more than one "unit" is described as being present, those units are operated in a parallel fashion unless otherwise stated. A single "unit", however, may comprise more than one of the units in series, or in parallel, depending on the context. For example, an acid gas removal unit may comprise a hydrogen sulfide removal unit followed in series by a carbon dioxide removal unit. As another example, a contaminant removal unit may comprise a first removal unit for a first contaminant followed in series by a second removal unit for a second contaminant. Yet another example, a compressor may comprise a first compressor to compress a stream to a first pressure, followed in series by a second compressor to further compress the stream to a second (higher) pressure.

The term "a portion of the carbonaceous feedstock" refers to carbon content of unreacted feedstock as well as partially reacted feedstock, as well as other components that may be derived in whole or part from the carbonaceous feedstock (such as carbon monoxide, hydrogen and methane). For example, "a portion of the carbonaceous feedstock" includes carbon content that may be present in by-product char and recycled fines, which char is ultimately derived from the original carbonaceous feedstock.

The term "superheated steam" in the context of the present invention refers to a steam stream that is non-condensing under the conditions utilized, as is commonly understood by persons of ordinary skill in the relevant art.

The term "steam demand" refers to the amount of steam that must be added to the various processes of this invention via the gas feed streams. For example, in the hydromethanation reactor steam is consumed in the hydromethanation reaction and some steam must be added to the hydromethanation reactor. The theoretical consumption of steam is two moles for every two moles of carbon in the feed to produce one mole of methane and one mole of carbon dioxide (see equation (V)). In actual practice, the steam consumption is not perfectly efficient and steam is withdrawn with the product gases; therefore, a greater than theoretical amount of steam needs to be added to the hydromethanation reactor, which added amount is the "steam demand". Steam can be added, for example, via a steam stream and an oxygen stream which are typically combined prior to introduction into the hydromethanation reactor (as shown in FIG. 1 and as discussed below). The amount of steam to be added (and the source) is discussed in further detail below. Steam generated in situ from the carbonaceous feedstock (e.g., from vaporization of any moisture content of the carbonaceous feedstock, or from an oxidation reaction with hydrogen, methane and/or other hydrocarbons present in or generated from the carbonaceous feedstock) can assist in providing steam; however, it should be noted that any steam generated in situ or fed into the hydromethanation reactor at a temperature lower than the operating temperature within the hydromethanation reactor (the hydromethanation reaction temperature) will have an impact on the "heat demand" for the hydromethanation reaction.

The term "heat demand" refers to the amount of heat energy that must be added to the hydromethanation reactor generated in situ (for example, via a combustion/oxidation reaction with supplied oxygen as discussed below) to keep the reaction of step (c) in substantial thermal balance, as further detailed below.

The term "power demand" refers to the amount of power that must be used to operate the processes of this invention.

Although methods and materials similar or equivalent to those described herein can be used in the practice or testing of the present disclosure, suitable methods and materials are described herein. The materials, methods, and examples herein are thus illustrative only and, except as specifically stated, are not intended to be limiting.

General Process Information

In one embodiment of the invention, a fines-cleaned methane-enriched product gas stream (70) and a carbon- and catalyst-depleted char stream (59) are ultimately generated from a non-gaseous carbonaceous material (10) and a hydromethanation catalyst (31) as illustrated in FIG. 1.

Referring to FIG. 1, in accordance with an embodiment of the invention, the non-gaseous carbonaceous material (10) is processed in a feedstock preparation unit (100) to generate a carbonaceous feedstock (32) which is fed to a catalyst application unit (350) where hydromethanation catalyst (31) is applied to generate a catalyzed carbonaceous feedstock (31+32). The application methods can include mechanical mixing devices to disperse the catalyst solution over the solid feed particles and thermal dryers to achieve the preferred moisture content for the catalyzed carbonaceous feedstocks (31+32).

The feedstock preparation unit (100) includes coal or coke pulverization machines to achieve a pre-determined optimal size distribution which largely depends on the carbonaceous mechanical and chemical properties. In some cases, pelletization and/or briquetting machines are included to consolidate fines to maximize the utilization of all solid feedstock materials.

The hydromethanation catalyst stream (31) will typically comprise a recovered hydromethanation catalyst stream (57) recovered from by-product char (54) and recovered secondary fines (66), and a make-up catalyst from a make-up catalyst stream (56).

The catalyzed carbonaceous feedstock (31+32) is fed into a hydromethanation reactor (200) along with steam stream (12a) and oxygen stream (15a).

Steam streams (12a) and (12b) are provided by a steam source such as steam distribution system (11), which desirably utilizes process heat recovery (e.g., heat energy recovery from the hot raw product gas and other process sources) such that the process is steam integrated and steam sufficient.

The steam stream (12a) and oxygen stream (15a) (from oxygen stream (15) having been split into oxygen streams (15a) and (15b)) may be a single feed stream which comprises, or multiple feed streams which comprise, in combination with the in situ generation of heat energy and syngas, steam, heat energy, as required to at least substantially satisfy, or at least satisfy, steam and heat demands of the hydromethanation reaction that takes place in hydromethanation reactor (200).

In the hydromethanation reactor (200), (i) a portion of the carbonaceous feedstock, steam, hydrogen and carbon monoxide react in the presence of the hydromethanation catalyst to generate a methane-enriched raw product gas (the hydromethanation reaction), and (ii) a portion of the carbonaceous feedstock reacts in the presence of steam and oxygen to generate heat energy and typically carbon monoxide, hydrogen and carbon dioxide. The generated methane-enriched raw product gas is withdrawn from the hydromethanation reactor (200) as a methane-enriched raw product gas stream (50). The withdrawn methane-enriched raw product gas stream (50) typically comprises at least methane, carbon monoxide, carbon dioxide, hydrogen, hydrogen sulfide, steam, entrained solids fines and heat energy.

The hydromethanation reactor (200) comprises a fluidized bed (202) having an upper portion (202b) above a lower portion (202a) and a disengagement zone (204) above the fluidized bed. Hydromethanation reactor (200) also typically comprises a gas mixing zone (206) below the fluidized-bed (202), with the two sections typically being separated by a grid plate (208) or similar divider (for example, an array of sparger pipes). Oxygen (15a) is mixed with the high-pressure, superheated steam (12a), and the mixture introduced into the gas mixing zone (206), into the lower portion (202a) of the fluidized bed (202) via the gas mixing zone (206), into the fluidized bed (202) at other locations, or into a combination thereof. Desirably, oxygen is fed into the lower portion of the fluidized bed. Without being bound by any particular theory, the hydromethanation reaction predominates in upper portion (202b), and an oxidation reaction with the oxygen from oxygen stream (15a) predominates in lower portion (202a). It is believed that there is no specific defined boundary between the two portions, but rather there is a transition as oxygen is consumed (and heat energy and syngas are generated) in lower portion (202a). It is also believed that oxygen consumption is rapid under the conditions present in hydromethanation reactor (200).

At least a portion of the carbonaceous feedstock in lower portion (202a) of fluidized bed (202) will react with oxygen from oxygen stream (15a) to generate heat energy, and hydrogen and carbon monoxide (syngas). This includes the reaction of solid carbon from unreacted (fresh) feedstock, partially reacted feedstock (such as char and recycled fines), as well as gases (carbon monoxide, hydrogen, methane and higher hydrocarbons) that may be generated from or carried with the feedstock and recycle fines in lower portion (202a). Generally, some water (steam) may be produced, as well as other by-products such as carbon dioxide depending on the extent of combustion/oxidation and the water gas shift reaction. As indicated above, in hydromethanation reactor (200) (predominantly in upper portion (202b) of fluidized bed (202)) the carbonaceous feedstock, steam, hydrogen and carbon monoxide react in the presence of the hydromethanation catalyst to generate a methane-enriched raw product, which is ultimately withdrawn as a methane-enriched raw product stream (50) from the hydromethanation reactor (200).

The reactions of the carbonaceous feedstock in fluidized bed (202) also result in a by-product char comprising unreacted carbon as well as non-carbon content from the carbonaceous feedstock (including hydromethanation catalyst). To prevent buildup of the residue in the hydromethanation reactor (200), a solid purge of by-product char (54) is routinely withdrawn (periodically or continuously) via a char withdrawal line (210). The by-product char (54) comprises a carbon content and entrained hydromethanation catalyst.

In one embodiment as disclosed in previously incorporated US2012/0102836A1, carbonaceous feedstock (32) (or catalyzed carbonaceous feedstock (31+32)) is fed into lower portion (202a) of fluidized bed (202). Because catalyzed carbonaceous feedstock (31+32) is introduced into lower portion (202a) of fluidized bed (202), at least one char withdrawal line (210) will typically be located at a point such that by-product char is withdrawn from fluidized bed (202) at one or more points above the feed location of catalyzed carbonaceous feedstock (31+32), typically from upper portion (202b) of fluidized bed (202).

Particles too large to be fluidized in fluidized-bed section (202), for example, large-particle by-product char and non-fluidizable agglomerates, are generally collected in lower portion (202a) of fluidized bed (202), as well as in gas mixing zone (206). Such particles will typically comprise a carbon content (as well as an ash and catalyst content), and may be removed periodically from hydromethanation reactor (200) via a char withdrawal line (210) for catalyst recovery and further processing.

All or a portion of by-product char stream (54) (typically all of such stream) is processed in a catalyst recovery unit (300) to recover entrained hydromethanation catalyst, and optionally other value-added by-products such as vanadium and nickel (depending on the content of the non-gaseous carbonaceous material (10)), to generate a carbon- and catalyst-depleted char stream (59) and a recovered hydromethanation catalyst stream (57).

The catalyst-depleted char stream (59) may be processed in a boiler to generate steam and power.

In hydromethanation reactor (200), the methane-enriched raw product gas typically passes through the disengagement zone (204) above the fluidized-bed section (202) prior to withdrawal from hydromethanation reactor (200). The disengagement zone (204) may optionally contain, for example, one or more internal cyclones and/or other entrained particle disengagement mechanisms (not shown). The "withdrawn" (see discussion below) methane-enriched raw product gas stream (50) typically comprises at least methane, carbon monoxide, carbon dioxide, hydrogen, hydrogen sulfide, steam, heat energy and entrained fines.

The methane-enriched raw product gas stream (50) is initially treated to remove a substantial portion of the entrained fines, typically via a cyclone assembly (for example, one or more internal and/or external cyclones), which may be followed if necessary by optional additional treatments such as venturi scrubbers, as discussed in more detail below. In the embodiment as shown in FIG. 1, the cyclone assembly comprises an external primary cyclone (360) followed by an external secondary cyclone (370), but other arrangements would be suitable as well. For example, the cyclone assembly could comprise an internal primary cyclone followed by an external secondary cyclone.

The "withdrawn" methane-enriched raw product gas stream (50), therefore, is to be considered the raw product prior to fines separation, regardless of whether the fines separation takes place internal to and/or external of hydromethanation reactor (200).

As specifically depicted in FIG. 1, the methane-enriched raw product stream (50) is passed from hydromethanation reactor (200) to an external primary cyclone (360) for separation of the predominant portion of entrained fines particles. While primary cyclone (360) is shown in FIG. 1 as a single external cyclone for simplicity, as indicated above cyclone assembly (360) may be an internal and/or external cyclone, and may also be a series of multiple internal and/or external cyclones.

As shown in FIG. 1, the methane-enriched raw product gas stream (50) is treated in primary cyclone (360) to generate a fines-depleted methane-enriched raw product gas stream (64) and a recovered primary fines stream (362).

Recovered primary fines stream (362) is fed back into hydromethanation reactor (200), for example, into one or more portions of fluidized bed (202) via fines recycle line (364). For example, as disclosed in previously incorporated US2012/0060417A1, recovered fines are fed back into lower portion (202*a*) of fluidized bed (202) via fines recycle line (364).

The fines-depleted methane-enriched raw product gas stream (64) typically comprises at least methane, carbon monoxide, carbon dioxide, hydrogen, hydrogen sulfide, steam, ammonia and heat energy, as well as small amounts of contaminants such as remaining residual entrained fines, and other volatilized and/or carried material that may be present in the carbonaceous feedstock. There are typically virtually no (total typically less than about 50 ppm) condensable (at ambient conditions) hydrocarbons present in fines-depleted methane-enriched raw product gas stream (64).

Typically, as shown in FIG. 1, the fines-depleted methane-enriched raw product gas stream (64) will be fed to a secondary cyclone (370) to remove a substantial portion of any remaining fines, generating a fines-cleaned methane-enriched raw product gas stream (70) and a recovered secondary fines stream (66). Recovered secondary fines stream (66) will typically be recycled back to catalyst recovery unit (300).

In one embodiment, all or a portion of a recovered secondary fines stream (66) may be co-processed with the withdrawn by-product char (54) in the catalyst recovery unit (300), or some combination thereof.

The catalyst recovery unit (300) recovers the water-soluble catalyst by conventional solids leaching or washing technologies. Unit (300) may include countercurrent mixer settlers or filter presses with wash zones or any combination of similar solid washing/leaching and dewatering devices. In particular, the catalyst recovery unit (300) may comprise a quench tank and a quench medium, the treatment comprising the steps of: quenching the by-product char stream (54) with the quench medium to extract a portion of the entrained catalyst to generate a carbon- and catalyst-depleted char and liberated hydromethanation catalyst; withdrawing a stream of carbon- and catalyst-depleted char from the catalyst recovery unit (300) as the carbon- and catalyst-depleted char stream (59); and withdrawing a stream of liberated hydromethanation catalyst from the catalyst recovery unit (300) as the recovered hydromethanation catalyst stream (57). The recovered secondary fines stream (66) is fed to the catalyst recovery unit (300).

The hydromethanation catalyst (31) will typically comprise at least a portion of the recovered hydromethanation catalyst stream (57) and a make-up catalyst from a make-up catalyst stream (56).

The fines-cleaned methane-enriched raw product gas stream (70) can be treated in one or more downstream processing steps to recover heat energy, decontaminate and convert, to one or more value-added products such as, for example, substitute natural gas (pipeline quality), hydrogen, carbon monoxide, syngas, ammonia, methanol and other syngas-derived products, electrical power and steam.

Additional details and embodiments are provided below.

Hydromethanation

In an embodiment in accordance with the present invention as illustrated in FIG. 1, catalyzed carbonaceous feedstock (31+32), steam stream (12*a*) and an oxygen stream (15*a*) are introduced into hydromethanation reactor (200).

Char by-product removal from hydromethanation reactor (200) can be at any desired place or places, for example, at the top of fluidized bed (202), at any place within upper portion (202*b*) and/or lower portion (202*a*) of fluidized bed (202), and/or at or just below grid plate (208). As indicated above, the location where catalyzed carbonaceous feedstock (31+32) is introduced will have an influence on the location of a char withdrawal point.

Typically, there will be at least one char withdrawal point at or below grid plate (208) to withdraw char comprising larger or agglomerated particles, as discussed above.

Hydromethanation reactor (200) is typically operated at moderately high pressures and temperatures, requiring introduction of solid streams (e.g., catalyzed carbonaceous feedstock (31+32) and if present recycle fines) to the reaction chamber of the reactor while maintaining the required temperature, pressure and flow rate of the streams. Those skilled in the art are familiar with feed inlets to supply solids into the reaction chambers having high pressure and/or temperature environments, including star feeders, screw feeders, rotary pistons and lock-hoppers. It should be understood that the feed inlets can include two or more pressure-balanced elements, such as lock hoppers, which would be used alternately. In some instances, the carbonaceous feedstock can be prepared at pressure conditions above the operating pressure of the reactor and, hence, the particulate composition can be directly passed into the reactor without further pressurization. Gas for pressurization can be an inert gas such as nitrogen, a reactive gas such as steam, or more typically a stream of carbon dioxide that can, for example be recycled from a carbon dioxide stream generated by the acid gas removal unit.

Hydromethanation reactor (200) is desirably operated at a moderate temperature (as compared to "conventional" oxidation-based gasification processes), with an operating temperature from about 800° F. (about 427° C.), or from about 1000° F. (about 538° C.), or from about 1100° F. (about 593° C.), or from about 1200° F. (about 649° C.), to about 1500° F. (about 816° C.), or to about 1400° F. (about 760° C.), or to about 1375° F. (about 746° C.); and a pressure of at least about 250 psig (about 1825 kPa, absolute), or at least about 400 psig (about 2860 kPa), or at least about 450 psig (about 3204 kPa). Typically, the pressure can range up to the levels of mechanical feasibility, for example, up to about 1200 psig (about 8375 kPa), up to about 1000 psig (about 6996 kPa), or to about 800 psig (about 5617 kPa), or to about 700 psig (about 4928 kPa), or to about 600 psig (about 4238 kPa), or to about 500 psig (about 3549 kPa). In one embodiment, hydromethanation reactor (200) is operated at a pressure (first operating pressure) of up to about 600 psig (about 4238 kPa), or up to about 550 psig (about 3894 kPa). In this case, the preferred pressure range may be below 550 psig (3894 kPa) but still above 100 psig (about 708 kPa)

Typical gas flow velocities in hydromethanation reactor (200) are from about 0.5 ft/sec (about 0.15 m/sec), or from about 1 ft/sec (about 0.3 m/sec), to about 2.0 ft/sec (about 0.6 m/sec), or to about 1.5 ft/sec (about 0.45 m/sec).

As oxygen stream (15a) is fed into hydromethanation reactor (200), a portion of the carbonaceous feedstock (desirably carbon from the partially reacted feedstock, by-product char and recycled fines) will be consumed in a partial oxidation/combustion reaction, generating heat energy as well as typically some amounts carbon monoxide and hydrogen (and typically other gases such as carbon dioxide and steam). The variation of the amount of oxygen supplied to hydromethanation reactor (200) provides an advantageous process control to ultimately maintain the syngas and heat balance. Increasing the amount of oxygen will increase the partial oxidation/combustion, and therefore increase in situ heat generation. Decreasing the amount of oxygen will conversely decrease the in situ heat generation.

The amount of oxygen supplied to hydromethanation reactor (200) must be sufficient to combust/oxidize enough of the carbonaceous feedstock to generate enough heat energy and syngas to meet the heat and syngas demands of the steady-state hydromethanation reaction.

In one embodiment, the total amount of molecular oxygen that is provided to the hydromethanation reactor (200) can range from about 0.10, or from about 0.20, or from about 0.25, to about 0.6, or to about 0.5, or to about 0.4, or to about 0.35 weight units (for example, pound or kg) of $O_2$ per weight unit (for example, pound or kg) of dry, catalyst-free carbonaceous feedstock (32).

The hydromethanation and oxidation/combustion reactions within hydromethanation reactor (200) will occur contemporaneously. Depending on the configuration of hydromethanation reactor (200), the two steps will typically predominate in separate zones—the hydromethanation in upper portion (202b) of fluidized bed (202), and the oxidation/combustion in lower portion (202a) of fluidized bed (202).

Oxygen stream (15a) is typically mixed with steam stream (12a) and the mixture introduced into fluidized bed (202), into gas mixing zone (206), into lower portion (202a) via gas mixing zone (206), into fluidized bed (202) at other locations, or a combination thereof. These streams are introduced at these locations in the hydromethanation reactor (200) to avoid formation of hot spots in the reactor, and to avoid (minimize) combustion of the desired gaseous products generated within hydromethanation reactor (200). Feeding the catalyzed carbonaceous feedstock (31+32) with an elevated moisture content, and particularly into lower portion (202a) of fluidized bed (202), also assists in heat dissipation and the avoidance of formation of hot spots in reactor (200), as disclosed in previously incorporated US2012/0102837A1.

Oxygen stream (15a) can be fed into hydromethanation reactor (200) by any suitable means such as direct injection of purified oxygen, oxygen-air mixtures, oxygen-steam mixtures, oxygen-carbon dioxide mixtures, or oxygen-inert gas mixtures into the reactor. See, for instance, U.S. Pat. No. 4,315,753 and Chiaramonte et al., Hydrocarbon Processing, September 1982, pp. 255-257. As shown in FIG. 1, oxygen stream (15a) is supplied by an air separation unit (14).

Oxygen stream (15a) is typically generated via standard air-separation technologies, and will be fed mixed with steam, and introduced at a pressure at least slightly higher than present in hydromethanation reactor (200).

As indicated above, the hydromethanation reaction has a steam demand, a heat demand and a syngas demand. These conditions in combination are important factors in determining the operating conditions for the hydromethanation reaction as well as the remainder of the process.

For example, the hydromethanation reaction requires a theoretical molar ratio of steam to carbon (in the feedstock) of at least about 1. Typically, however, the molar ratio is greater than about 1, or from about 1.5 (or greater), to about 6 (or less), or to about 5 (or less), or to about 4 (or less), or to about 3 (or less), or to about 2 (or less). The moisture content of the catalyzed carbonaceous feedstock (31+32), moisture generated from the carbonaceous feedstock in the hydromethanation reactor (200), and steam included in the steam stream (12a), oxygen stream (15a), and recycle fines stream(s) all contribute steam for the hydromethanation reaction. The steam in steam stream (12a), oxygen stream (15a) and oxidation gas stream (52) should be sufficient to at least substantially satisfy (or at least satisfy) the "steam demand" of the hydromethanation reaction. The optimal amount of steam supplied to the reactor depends on many factors, for example, the elemental composition of the feedstock (C,H,N,O,S), the inorganic or ash content of the feedstock, the desired carbon conversion, the moisture content of the feed, the steam to dry feed ratio, the internal temperature and pressure of the reaction vessel, and the desired syngas composition.

As also indicated above, the hydromethanation reaction is essentially thermally balanced but, due to process heat losses and other energy requirements (for example, vaporization of moisture on the feedstock), some heat must be generated in situ (in hydromethanation reactor (200)) to maintain the thermal balance (the heat demand). The partial combustion/oxidation of carbon in the presence of the oxygen introduced into hydromethanation reactor (200) from oxygen stream (15a) should be sufficient to at least substantially satisfy (or at least satisfy) both the heat and syngas demand of the hydromethanation reaction.

The gas utilized in hydromethanation reactor (200) for pressurization and reaction of the catalyzed carbonaceous feedstock (31+32) comprises the steam stream (12a), oxygen stream (15a) and carbon dioxide transport gas, which can be supplied to hydromethanation reactor (200) according to methods known to those skilled in the art. Consequently, steam stream (12a) and oxygen stream (15a) must be provided at a higher pressure which allows them to enter hydromethanation reactor (200).

Steam stream (12a) can be at a temperature as low as the saturation point at the feed pressure, but it is desirable to feed at a temperature above this to avoid the possibility of any condensation occurring. Typical feed temperatures of superheated steam stream (12a) are from about 500° F. (about 260° C.), or from about 600° F. (about 316° C.), or from about 700° F. (about 371° C.), to about 950° F. (about 510° C.), or to about 900° F. (about 482° C.). Typical feed pressures of steam stream (12a) are about 25 psi (about 172 kPa) or greater than the pressure within hydromethanation reactor (200).

The actual temperature and pressure of steam stream (12a) will ultimately depend on the level of heat recovery from the process and the operating pressure within hydromethanation reactor (200), as discussed below. In any event, desirably no fuel-fired superheater should be used in the superheating of steam stream (12a) in steady-state operation of the process.

When steam stream (12a) and oxygen stream (15a) are combined for feeding into lower section (202a) of fluidized bed (202), the temperature of the combined stream will be controlled by the temperature of steam stream (12a), and will typically range from about 400° F. (about 204° C.), or from about 450° F. (about 232° C.), to about 650° F. (about 343° C.), or to about 600° F. (about 316° C.).

The temperature in hydromethanation reactor (200) can be controlled, for example, by controlling the amount and temperature of steam stream (12a) supplied to hydromethanation reactor (200).

Figure 2:
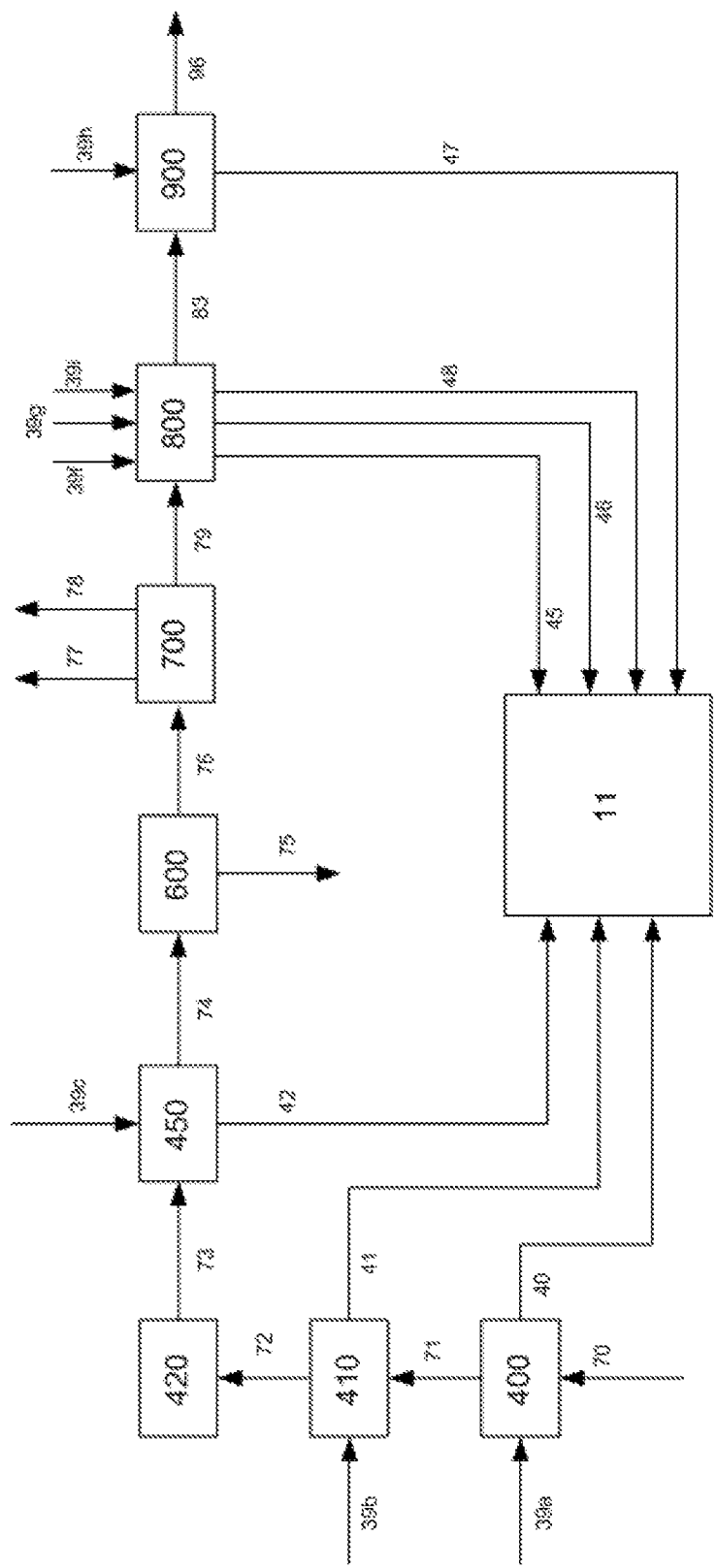
FIG. 2 is a schematic representation of the gas processing steps involved in converting the fines-depleted methane-rich raw gas stream to methanol. These steps include cooling the gas to ambient conditions while simultaneously recovering waste heat as superheated, high-pressure steam and saturated medium-pressure steam, removal of acid gases (mainly carbon dioxide and hydrogen sulfide), ammonia recovery, an autothermal reformer and a methanol synthesis loop with methanol purification.
Figure 3:
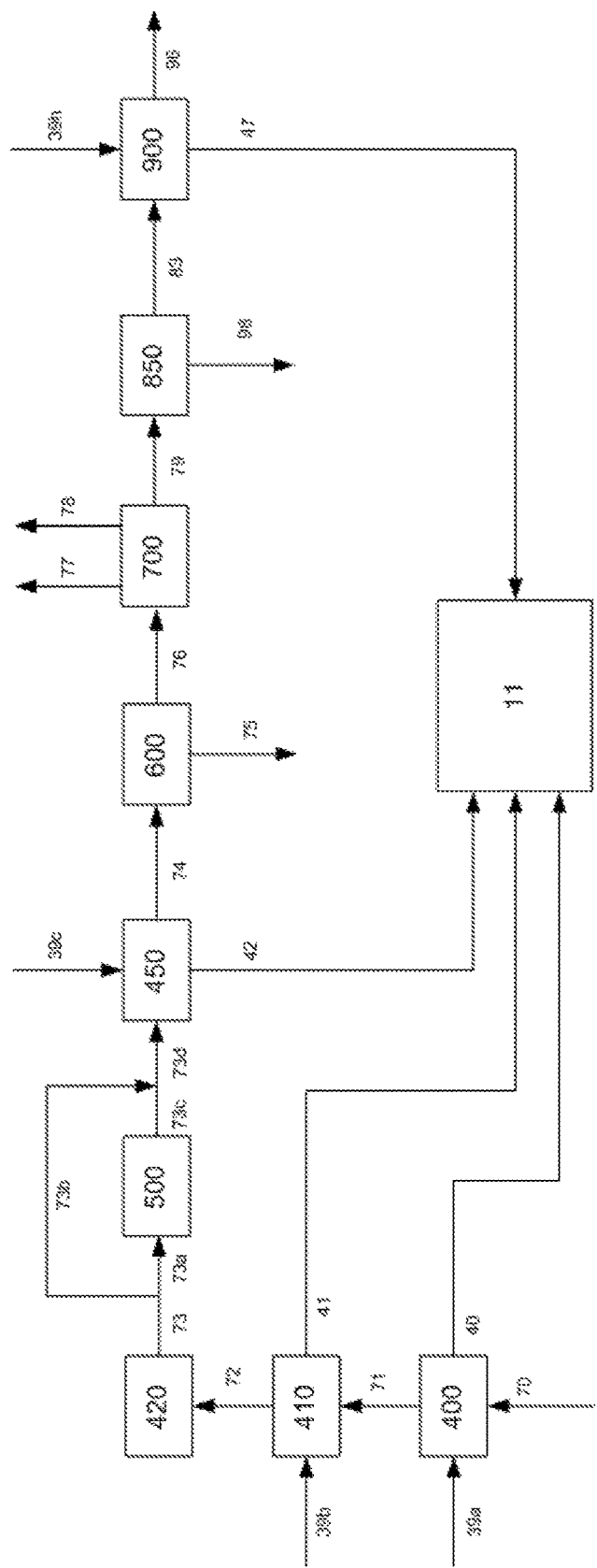
FIG. 3 is a schematic representation of a special case of the invention that allows co-production of methanol and substitute natural gas or liquefied natural gas through cryogenic liquefaction.

In steady-state operation, steam for hydromethanation reactor (200) is desirably solely generated from other process operations through process heat capture (such as generated in a waste heat boiler, generally referred to as "process steam" or "process-generated steam", and referenced in FIG. 1 as steam distribution system (11)), specifically from the cooling of the raw product gas in a heat exchanger unit. Additional steam can be generated for other portions of the overall process, such as disclosed, for example, in previously incorporated US2010/0287835A1 and US2012/0046510A1, and as shown in FIGS. 2 and 3 discussed below.

The overall process described herein is desirably steam positive, such that steam demand (pressure and amount) for hydromethanation reactor (200) can be satisfied via heat exchange and with process heat recovery at the different stages allowing for production of excess steam that can be used for power generation and other purposes. Desirably, process-generated steam from accounts for 100 wt % or greater of the steam demand of the hydromethanation reaction.

The result of the hydromethanation reaction is a methane-enriched raw product, which is withdrawn from hydromethanation reactor (200) as methane-enriched raw product stream (50) typically comprising $CH_4$, $CO_2$, $H_2$, CO, $H_2S$, unreacted steam, heat energy and, optionally, other contaminants such as entrained fines, $NH_3$, COS, and HCN depending on the nature of the carbonaceous material utilized for hydromethanation.

The non-gaseous carbonaceous materials (10) useful in these processes include, for example, a wide variety of biomass and non-biomass materials. The carbonaceous feedstock (32) is derived from one or more non-gaseous carbonaceous materials (10), which are processed in a feedstock preparation unit (100) as discussed below.

The hydromethanation catalyst (31) can comprise one or more catalyst species such as alkali metals or alkali metal compounds. Suitable alkali metals are lithium, sodium, potassium, rubidium, cesium, and mixtures thereof. Particularly useful are potassium sources. Suitable alkali metal compounds include alkali metal carbonates, bicarbonates, formates, oxalates, amides, hydroxides, acetates, or similar compounds. For example, the catalyst can comprise one or more of sodium carbonate, potassium carbonate, rubidium carbonate, lithium carbonate, cesium carbonate, sodium hydroxide, potassium hydroxide, rubidium hydroxide or cesium hydroxide, and particularly, potassium carbonate and/or potassium hydroxide.

The carbonaceous feedstock (32) and the hydromethanation catalyst (31) are typically intimately mixed (i.e., to provide a catalyzed carbonaceous feedstock (31+32)) before provision to the hydromethanation reactor (200), but they can be fed separately as well.

The hot gas effluent leaving the reaction chamber of the hydromethanation reactor (200) can pass through a fines remover unit (such as cyclone assembly (360)), incorporated into and/or external of the hydromethanation reactor (200), which serves as a disengagement zone. Particles too heavy to be entrained by the gas leaving the hydromethanation reactor (200) (i.e., fines) are returned to the hydromethanation reactor (200), for example, to the reaction chamber (e.g., fluidized bed (202)).

Residual entrained fines are substantially removed by any suitable device such as internal and/or external cyclone separators or a mechanical filter, optionally followed by scrubbers. As discussed above, at least a portion of these fines can be returned to fluidized bed (202) via recycle line (364). Any remaining recovered fines can be processed to recover alkali metal catalyst, and/or combined at some stage with carbonaceous feedstock (32), and/or directly recycled back to feedstock preparation as described in previously incorporated US2009/0217589A1.

Removal of a "substantial portion" of fines means that an amount of fines is removed from the resulting gas stream such that downstream processing is not adversely affected; thus, at least a substantial portion of fines should be removed. Some minor level of ultrafine material may remain in the resulting gas stream to the extent that downstream processing is not significantly adversely affected. Typically, at least about 90 wt %, or at least about 95 wt %, or at least about 98 wt %, of the fines of a particle size greater than about 20 µm, or greater than about 10 µm, or greater than about 5 µm, are removed.

Additional residual entrained fines may be removed from the fines-depleted methane-enriched raw product gas stream (64) by any suitable device such as internal and/or external cyclone separators such as external secondary cyclone (370), optionally followed by scrubbers. The resulting fines-cleaned methane-enriched raw product stream (70) can be further processed for heat recovery and/or purification/conversion as required to achieve a desired product, as disclosed in the previously incorporated disclosures. Reference may be had to those disclosures for further details.

Catalyzed Carbonaceous Feedstock Preparation (100)

(a) Carbonaceous Materials Processing

Carbonaceous materials, such as biomass and non-biomass, can be prepared via crushing and/or grinding, either separately or together, according to any methods known in the art, such as impact crushing and wet or dry grinding to yield one or more carbonaceous particulates. Depending on the method utilized for crushing and/or grinding of the carbonaceous material sources, the resulting carbonaceous particulates may be sized (i.e., separated according to size) to provide a processed feedstock for use in catalyst loading processes to form a catalyzed carbonaceous feedstock.

Any method known to those skilled in the art can be used to size the particulates. For example, sizing can be performed by screening or passing the particulates through a screen or number of screens. Screening equipment can include grizzlies, bar screens, and wire mesh screens. Screens can be static or incorporate mechanisms to shake or vibrate the screen. Alternatively, classification can be used to separate the carbonaceous particulates. Classification equipment can include ore sorters, gas cyclones, hydrocyclones, rake classifiers, rotating trommels or fluidized classifiers. The carbonaceous materials can be also sized or classified prior to grinding and/or crushing.

The carbonaceous particulate can be supplied as a fine particulate having an average particle size of from about 25 microns, or from about 45 microns, up to about 2500 microns, or up to about 500 microns. One skilled in the art can readily determine the appropriate particle size for the carbonaceous particulates. For example, when a fluid bed catalytic gasifier is used, such carbonaceous particulates can have an average particle size which enables incipient fluidization of the carbonaceous materials at the gas velocity used in the fluid bed catalytic gasifier.

Additionally, certain carbonaceous materials, for example, corn stover and switchgrass, and industrial wastes, such as saw dust, either may not be amenable to crushing or grinding operations, or may not be suitable for use in the catalytic gasifier, for example due to ultra-fine particle sizes. Such materials may be formed into pellets or briquettes of a suitable size for crushing or for direct use in, for example, a fluid bed catalytic gasifier. Generally, pellets can be prepared by compaction of one or more carbonaceous material, see for example, previously incorporated US2009/0218424A1. In other examples, a biomass material and a coal can be formed into briquettes as described in U.S. Pat. Nos. 4,249,471, 4,152,119 and U.S. Pat. No. 4,225,457. Such pellets or briquettes can be used interchangeably with the preceding carbonaceous particulates in the following discussions.

Additional feedstock processing steps may be necessary depending on the qualities of carbonaceous material sources. Biomass may contain high moisture contents, such as green plants and grasses, and may require drying prior to crushing. Municipal wastes and sewages also may contain high moisture contents which may be reduced, for example, by use of a press or roll mill (e.g., U.S. Pat. No. 4,436,028). Likewise, non-biomass such as high-moisture coal, can require drying prior to crushing. Some caking coals can require partial oxidation to simplify catalytic gasifier operation. Non-biomass feedstocks deficient in ion-exchange sites, such as anthracites or petroleum cokes, can be pre-treated to create additional ion-exchange sites to facilitate catalyst loading and/or association. Such pre-treatments can be accomplished by any method known to the art that creates ion-exchange capable sites and/or enhances the porosity of the feedstock (see, for example, previously incorporated U.S. Pat. No. 4,468,231 and GB1599932). Oxidative pre-treatment can be accomplished using any oxidant known to the art.

The ratio of the carbonaceous materials in the carbonaceous particulates can be selected based on technical considerations, processing economics, availability, and proximity of the non-biomass and biomass sources. The availability and proximity of the sources for the carbonaceous materials can affect the price of the feeds, and thus the overall production costs of the catalytic gasification process. For example, the biomass and the non-biomass materials can be blended in at about 5:95, about 10:90, about 15:85, about 20:80, about 25:75, about 30:70, about 35:65, about 40:60, about 45:55, about 50:50, about 55:45, about 60:40, about 65:35, about 70:20, about 75:25, about 80:20, about 85:15, about 90:10, or about 95:5 by weight on a wet or dry basis, depending on the processing conditions.

Significantly, the carbonaceous material sources, as well as the ratio of the individual components of the carbonaceous particulates, for example, a biomass particulate and a non-biomass particulate, can be used to control other material characteristics of the carbonaceous particulates. Non-biomass materials, such as coals, and certain biomass materials, such as rice hulls, typically include significant quantities of inorganic matter including calcium, alumina and silica which form inorganic oxides (i.e., ash) in the catalytic gasifier. At temperatures above about 500° C. to about 600° C., potassium and other alkali metals can react with the alumina and silica in ash to form insoluble alkali aluminosilicates. In this form, the alkali metal is substantially water-insoluble and inactive as a catalyst. To prevent buildup of the residue in the catalytic gasifier, a solid purge of char comprising ash, unreacted carbonaceous material, and various alkali metal compounds (both water soluble and water insoluble) can be routinely withdrawn.

In preparing the carbonaceous particulates, the ash content of the various carbonaceous materials can be selected to be, for example, about 20 wt % or less, or about 15 wt % or less, or about 10 wt % or less, or about 5 wt % or less, depending on, for example, the ratio of the various carbonaceous materials and/or the starting ash in the various carbonaceous materials. In other embodiments, the resulting the carbonaceous particulates can comprise an ash content ranging from about 5 wt %, or from about 10 wt %, to about 20 wt %, or to about 15 wt %, based on the weight of the carbonaceous particulate. In other embodiments, the ash content of the carbonaceous particulate can comprise less than about 20 wt %, or less than about 15 wt %, or less than about 10 wt %, or less than about 8 wt %, or less than about 6 wt % alumina, based on the weight of the ash. In certain embodiments, the carbonaceous particulates can comprise an ash content of less than about 20 wt %, based on the weight of processed feedstock where the ash content of the carbonaceous particulate comprises less than about 20 wt % alumina, or less than about 15 wt % alumina, based on the weight of the ash.

Such lower alumina values in the carbonaceous particulates allow for, ultimately, decreased losses of alkali catalysts in the catalytic gasification portion of the process. As indicated above, alumina can react with alkali source to yield an insoluble char comprising, for example, an alkali aluminate or aluminosilicate. Such insoluble char can lead to decreased catalyst recovery (i.e., increased catalyst loss), and thus, require additional costs of make-up catalyst in the overall gasification process.

Additionally, the resulting carbonaceous particulates can have a significantly higher % carbon, and thus btu/lb value and methane product per unit weight of the carbonaceous particulate. In certain embodiments, the resulting carbonaceous particulates can have a carbon content ranging from about 75 wt %, or from about 80 wt %, or from about 85 wt %, or from about 90 wt %, up to about 95 wt %, based on the combined weight of the non-biomass and biomass.

In one example, a non-biomass and/or biomass is wet ground and sized (e.g., to a particle size distribution of from about 25 to about 2500 µm) and then drained of its free water (i.e., dewatered) to a wet cake consistency. Examples of suitable methods for the wet grinding, sizing, and dewatering are known to those skilled in the art; for example, see previously incorporated US2009/0048476A1. The filter cakes of the non-biomass and/or biomass particulates formed by the wet grinding in accordance with one embodiment of the present disclosure can have a moisture content ranging from about 40% to about 60%, or from about 40% to about 55%, or below 50%. It will be appreciated by one of ordinary skill in the art that the moisture content of dewatered wet ground carbonaceous materials depends on the particular type of carbonaceous materials, the particle size distribution, and the particular dewatering equipment used. Such filter cakes can be thermally treated, as described herein, to produce one or more reduced moisture carbonaceous particulates which are passed to the feedstock preparation unit (100).

Each of the one or more carbonaceous particulates can have a unique composition, as described above. For example, two carbonaceous particulates can be utilized, where a first carbonaceous particulate comprises one or more biomass materials and the second carbonaceous particulate comprises one or more non-biomass materials. Alternatively, a single carbonaceous particulate comprising one or more carbonaceous materials utilized.

(b) Catalyst Loading

The one or more carbonaceous particulates are further processed to associate at least one gasification catalyst, typically comprising a source of at least one alkali metal, to generate the catalyzed carbonaceous feedstock (31+32).

The carbonaceous particulate provided for catalyst loading can be either treated to form a catalyzed carbonaceous feedstock (31+32) which is passed to the hydromethanation reactor (200), or split into one or more processing streams, where at least one of the processing streams is associated with a gasification catalyst to form at least one catalyst-treated feedstock stream. The remaining processing streams can be, for example, treated to associate a second component therewith. Additionally, the catalyst-treated feedstock stream can be treated a second time to associate a second component therewith. The second component can be, for example, a second gasification catalyst, a co-catalyst, or other additive.

In one example, the primary gasification catalyst can be provided to the single carbonaceous particulate (e.g., a potassium and/or sodium source), followed by a separate treatment to provide one or more co-catalysts and additives (e.g., a calcium source) to the same single carbonaceous particulate to yield the catalyzed carbonaceous feedstock (31+32). For example, see previously incorporated US2009/0217590A1 and US2009/0217586A1. The gasification catalyst and second component can also be provided as a mixture in a single treatment to the single carbonaceous particulate to yield the catalyzed carbonaceous feedstock (31+32).

When one or more carbonaceous particulates are provided for catalyst loading, then at least one of the carbonaceous particulates is associated with a gasification catalyst to form at least one catalyst-treated feedstock stream. Further, any of the carbonaceous particulates can be split into one or more processing streams as detailed above for association of a second or further component therewith. The resulting streams can be blended in any combination to provide the catalyzed carbonaceous feedstock (31+32), provided at least one catalyst-treated feedstock stream is utilized to form the catalyzed feedstock stream.

In one embodiment, at least one carbonaceous particulate is associated with a gasification catalyst and optionally, a second component. In another embodiment, each carbonaceous particulate is associated with a gasification catalyst and optionally, a second component.

Any methods known to those skilled in the art can be used to associate one or more gasification catalysts with any of the carbonaceous particulates and/or processing streams. Such methods include but are not limited to, admixing with a solid catalyst source and impregnating the catalyst onto the processed carbonaceous material. Several impregnation methods known to those skilled in the art can be employed to incorporate the gasification catalysts. These methods include but are not limited to, incipient wetness impregnation, evaporative impregnation, vacuum impregnation, dip impregnation, ion exchanging, and combinations of these methods.

In one embodiment, an alkali metal gasification catalyst can be impregnated into one or more of the carbonaceous particulates and/or processing streams by slurrying with a solution (e.g., aqueous) of the catalyst in a loading tank. When slurried with a solution of the catalyst and/or co-catalyst, the resulting slurry can be dewatered to provide a catalyst-treated feedstock stream, again typically, as a wet cake. The catalyst solution can be prepared from any catalyst source in the present processes, including fresh or make-up catalyst and recycled catalyst or catalyst solution. Methods for dewatering the slurry to provide a wet cake of the catalyst-treated feedstock stream include filtration (gravity or vacuum), centrifugation, and a fluid press.

One particular method suitable for combining a coal particulate and/or a processing stream comprising coal with a gasification catalyst to provide a catalyst-treated feedstock stream is via ion exchange as described in previously incorporated US2009/0048476A1. Catalyst loading by ion exchange mechanism can be maximized based on adsorption isotherms specifically developed for the coal, as discussed in the incorporated reference. Such loading provides a catalyst-treated feedstock stream as a wet cake. Additional catalyst retained on the ion-exchanged particulate wet cake, including inside the pores, can be controlled so that the total catalyst target value can be obtained in a controlled manner. The catalyst loaded and dewatered wet cake may contain, for example, about 50 wt % moisture. The total amount of catalyst loaded can be controlled by controlling the concentration of catalyst components in the solution, as well as the contact time, temperature and method, as can be readily determined by those of ordinary skill in the relevant art based on the characteristics of the starting coal.

In another example, one of the carbonaceous particulates and/or processing streams can be treated with the gasification catalyst and a second processing stream can be treated with a second component (see previously incorporated US2007/0000177A1).

The carbonaceous particulates, processing streams, and/or catalyst-treated feedstock streams resulting from the preceding can be blended in any combination to provide the catalyzed carbonaceous feedstock, provided at least one catalyst-treated feedstock stream is utilized to form the catalyzed carbonaceous feedstock (31+32). Ultimately, the catalyzed carbonaceous feedstock (31+32) is passed onto the hydromethanation reactor (200).

Generally, each feedstock preparation unit (100) comprises at least one loading tank to contact one or more of the carbonaceous particulates and/or processing streams with a solution comprising at least one gasification catalyst, to form one or more catalyst-treated feedstock streams. Alternatively, the catalytic component may be blended as a solid particulate into one or more carbonaceous particulates and/or processing streams to form one or more catalyst-treated feedstock streams.

Typically, the gasification catalyst is present in the catalyzed carbonaceous feedstock in an amount sufficient to provide a ratio of alkali metal atoms to carbon atoms in the particulate composition ranging from about 0.01, or from about 0.02, or from about 0.03, or from about 0.04, to about 0.10, or to about 0.08, or to about 0.07, or to about 0.06.

With some feedstocks, the alkali metal component may also be provided within the catalyzed carbonaceous feedstock to achieve an alkali metal content of from about 3 to about 10 times more than the combined ash content of the carbonaceous material in the catalyzed carbonaceous feedstock, on a mass basis.

Suitable alkali metals are lithium, sodium, potassium, rubidium, cesium, and mixtures thereof. Particularly useful are potassium sources. Suitable alkali metal compounds include alkali metal carbonates, bicarbonates, formates, oxalates, amides, hydroxides, acetates, or similar compounds. For example, the catalyst can comprise one or more of sodium carbonate, potassium carbonate, rubidium carbonate, lithium carbonate, cesium carbonate, sodium hydroxide, potassium hydroxide, rubidium hydroxide or cesium hydroxide, and particularly, potassium carbonate and/or potassium hydroxide.

Optional co-catalysts or other catalyst additives may be utilized, such as those disclosed in the previously incorporated references.

The one or more catalyst-treated feedstock streams that are combined to form the catalyzed carbonaceous feedstock (31+32) typically comprise greater than about 50%, greater than about 70%, or greater than about 85%, or greater than about 90% of the total amount of the loaded catalyst associated with the catalyzed carbonaceous feedstock (31+32). The percentage of total loaded catalyst that is associated with the various catalyst-treated feedstock streams can be determined according to methods known to those skilled in the art.

Separate carbonaceous particulates, catalyst-treated feedstock streams, and processing streams can be blended appropriately to control, for example, the total catalyst loading or other qualities of the catalyzed carbonaceous feedstock (31+32), as discussed previously. The appropriate ratios of the various stream that are combined will depend on the qualities of the carbonaceous materials comprising each as well as the desired properties of the catalyzed carbonaceous feedstock (31+32). For example, a biomass particulate stream and a catalyzed non-biomass particulate stream can be combined in such a ratio to yield a catalyzed carbonaceous feedstock (31+32) having a predetermined ash content, as discussed previously.

Any of the preceding catalyst-treated feedstock streams, processing streams, and processed feedstock streams, as one or more dry particulates and/or one or more wet cakes, can be combined by any methods known to those skilled in the art including, but not limited to, kneading, and vertical or horizontal mixers, for example, single or twin screw, ribbon, or drum mixers. The resulting catalyzed carbonaceous feedstock (31+32) can be stored for future use or transferred to one or more feed operations for introduction into the catalytic gasifiers. The catalyzed carbonaceous feedstock can be conveyed to storage or feed operations according to any methods known to those skilled in the art, for example, a screw conveyer or pneumatic transport.

Further, excess moisture can be removed from the catalyzed carbonaceous feedstock (31+32). For example, the catalyzed carbonaceous feedstock (31+32) may be dried with a fluid bed slurry drier (i.e., treatment with superheated steam to vaporize the liquid), or the solution thermally evaporated or removed under a vacuum, or under a flow of an inert gas, to provide a catalyzed carbonaceous feedstock having a residual moisture content, for example, of about 10 wt % or less, or of about 8 wt % or less, or about 6 wt % or less, or about 5 wt % or less, or about 4 wt % or less.

Production of Methanol Via Autothermal Reformer

Gas Processing—Heat Exchanger System (400) and High-Pressure Steam Stream (40)

The fines-cleaned methane-enriched raw product gas stream (70) leaving the hydromethanation reactor (200) contains a very small quantity of fines after being processed by the highly-efficient system of cyclones (360+370). The temperature and pressure of stream (70) are dictated by the chosen operating conditions. The pressure ranges from 250 to 1000 psig (1825 to 6996 kPa) and is preferably between 500 and 650 psig (3549 to 4583 kPa). The temperature ranges from 1100 to 1500° F. (593 to 816° C.) and is preferably between 1250 and 1350° F. (677 to 732° C.).

Referring to FIG. 2, fines-cleaned methane-enriched raw product gas stream (70) is routed to a heat exchanger or boiler system (400), optionally comprising a superheater section (not shown), to recover thermal energy in the form of high-pressure steam stream (40) by vaporization of boiler feed water (39a). The pressure of the steam is at least 25 to 50 psig (172 to 345 kPa) higher than the pressure of the hydromethanation reactor (200). Steam stream (40) is preferably superheated to 750 to 950° F. (399 to 510° C.) to maximize the thermal efficiency of the hydromethanation reactor (200). In the absence of the superheater section of heat exchanger system (400), saturated steam may be produced at the pressure of the heat exchanger system (400). High-pressure steam stream (40) is sent to the steam distribution system (11).

Cooled stream (71) is the methane-enriched raw product leaving the heat exchanger system (400) having been cooled to about 550° F. (288° C.). It is further cooled against boiler feed water (39b) to 370-400° F. (188 to 204° C.) in intermediate-pressure heat exchanger or boiler (410) to generate cooled stream (72) and intermediate-pressure saturated steam (41) at 150 psig (1136 kPa), which is close to the dew point of cooled stream (72) under those conditions. Intermediate-pressure saturated steam stream (41) is sent to the steam distribution system (11).

Cooled stream (72) leaving intermediate-pressure boiler (410) is scrubbed in the hot gas scrubber (420) with recycled process condensate (not shown), which is obtained from the low-temperature gas cooling system (450) and the ammonia recovery system (600) (as discussed below), to remove any traces of fine particulate matter that has escaped the cyclones. A bleed stream (not shown) from the hot gas scrubber (420) containing the fine particulate matter is routed to the catalyst recovery system (300) (see FIG. 1). A particle-depleted cooled gas (73) exits the hot gas scrubber (420).

Gas Conversion/Purification

The processing steps for further conversion of the particle-depleted cooled gas (73) will depend on the desired end products i.e. methanol or dual production of methanol and substitute natural gas. Referring to FIG. 2, the required processing steps for producing methanol comprise low temperature gas cooling (450), ammonia recovery (600), acid gas removal (700), autothermal reforming (800) and methanol synthesis (900).

(a) Low-Temperature Gas Cooling (450)

Particle-depleted cooled gas stream (73) exiting the hot gas scrubber (420) directly enters the low-temperature gas cooling system (450) and is cooled in a series of heat exchangers within low-temperature gas cooling system (450) to further reduce the temperature to 120° F. (49° C.) to produce a dry raw gas, cooled effluent stream (74). The low-temperature gas cooling system (450) will typically comprise first and second knock-out drums, an air cooler, and a trim cooler.

Particle-depleted cooled gas stream (73), initially at about 475° F. (246° C.), is first cooled against boiler feed water (39c) to generate medium-pressure steam (42) at 50 psig (446 kPa) and low-pressure steam (not shown) at two levels: 30 psig (308 kPa) and 15 psig (205 kPa). Recovery of low-grade heat allows heat integration with other parts of the process where steam at these pressure levels is needed. Medium-pressure steam stream (42) is sent to the steam distribution system (11). As the gas (73) is cooled down to 200° F. (93° C.), it begins to approach the water dew-point and the condensing water is recovered in a first knock-out drum (not shown). Further cooling of cooled effluent stream (74) takes place against the air cooler (not shown), which uses ambient air as a cooling medium, and finally the trim cooler (not shown), to achieve a final temperature of 120° F. (49° C.) using cooling water. Ambient conditions at the location of the low-temperature gas cooling system (450) will dictate the amount of air cooling and trim cooling that can be achieved. The stream leaving the trim cooler is sent to the second knock-out drum (not shown) to separate the remaining water from the stream (74). The combined condensate from the knock-out drums (not shown) is sent to the ammonia recovery system (600). Stream (74) exits the low-temperature gas cooling system (450).

(b) Ammonia Recovery System (600)

The low-temperature operation of the hydromethanation reactor (200) under highly reducing conditions relative to other gasification technologies allows all the nitrogen released as ammonia during devolatilization to remain in molecular form without converting to other nitrogen oxides or decomposing to gaseous nitrogen. Ammonia can be recovered according to methods known to those skilled in the art. A particular embodiment of the ammonia recovery process is described next.

Continuing to refer to FIG. 2, after cooled effluent stream (74) exits low-temperature gas cooling system (450) it is treated in an ammonia recovery system (600) to form an ammonia-depleted effluent (76). Ammonia is recovered from stream (74) by first washing stream (74) with chilled water at 50° F. (10° C.) to remove a majority of the ammonia. The resulting ammonia scrubber bottoms liquid is combined with the condensate from the knock-out drums and fed to a series of sour water strippers (not shown) that separate the ammonia from liquid-phase as a primary product stream and an off-gas containing trace amounts of ammonia, hydrogen cyanide, hydrogen sulfide and carbonyl sulfide. The off-gas stream is sent to the Claus unit (not shown) for further treatment.

The clean water leaving the sour-water strippers is devoid of dissolved gases. A portion of this water is utilized as a liquid feed for the hot gas scrubber (420). The balance of the water is sent to the catalyst recovery system (300) as a solvent for the char washing step (not shown).

Ammonia recovery is greater than 95% of the ammonia contained in the methane-rich raw gas stream. Ammonia is typically recovered as an aqueous solution (75) of concentration 20-30 wt %. Any recovered ammonia can be used as such or, for example, can be converted with other by-products from the process. For example, it may be reacted with sulfuric acid to generate ammonium sulfate as a product.

(c) Acid Gas Removal System (700)

Continuing to refer to FIG. 2, the effluent (76) leaving the ammonia recovery system (600) is subsequently fed to an acid gas removal (AGR) unit (700) to remove a substantial portion of $CO_2$ (77) and a substantial portion of the $H_2S$ (78) and generate a sweetened gas stream (79).

Acid gas removal processes typically involve contacting a gas stream with a solvent that selectively absorbs the acid gases. Several acid gas removal processes are commercially available and applicable for treatment of ammonia-depleted effluent (76). The main criteria for selection of the AGR are minimization of methane losses such that the sweetened gas stream (79) comprises at least a substantial portion (and substantially all) of the methane from the effluent stream (76) fed into acid gas removal unit (700). Typically, such losses should be about 2 mol % or less, or about 1.5 mol % or less, or about 1 mol % of less, respectively, of the methane feed to the AGR.

A solvent that meets the above criteria is refrigerated methanol. A commercially available process employing methanol as solvent is known by the trade-name Rectisol® and is offered by Linde AG and Lurgi Oel-Gas-Chemie GmbH. Another commercial process that may be considered is Selexol® (UOP LLC, Des Plaines, Ill. USA), which uses a proprietary solvent (dimethyl ether of polyethylene glycol). Similarly, a chemical solvent comprised of methyldiethanolamine (MDEA) with other additives such as piperazine may also be used. MDEA is available from process licensors such as BASF and Dow.

One method for removing acid gases is described in previously incorporated US2009/0220406A1.

At least a substantial portion (e.g., substantially all) of the $CO_2$ and/or $H_2S$ (and other remaining trace contaminants) should be removed via the acid gas removal processes. "Substantial" removal in the context of acid gas removal means removal of a high enough percentage of the component such that a desired product can be generated. The actual amounts of removal may thus vary from component to component. Only trace amounts (at most) of $H_2S$ can be present, although higher (but still small) amounts of $CO_2$ may be tolerable.

The resulting sweetened gas stream (79) will generally comprise hydrogen, carbon monoxide and methane (for the downstream methanation), and typically traces of $H_2O$. The sweetened gas (79) typically has a molar ratio of hydrogen to carbon monoxide of at least 1.5, and has greater than 25% methane on a dry, $CO_2$-free basis.

Any recovered $H_2S$ (78) from the acid gas removal (and other processes such as sour water stripping) can be converted to elemental sulfur by any method known to those skilled in the art, including the Claus process. Sulfur can be recovered as a molten liquid.

Any recovered $CO_2$ (77) from the acid gas removal can be compressed for transport in $CO_2$ pipelines, industrial use, and/or sequestration for storage or other processes such as enhanced oil recovery, and can also be used for other process operations (such as in certain aspects catalyst recovery and feed preparation).

(d) Autothermal Reformer (800) and Methanol Synthesis (900) Treatments

The resulting sweetened gas stream (79) can be further processed by autothermal reformer (800) treatment (utilizing boiler feed water (39*f*), (39*g*) and (39*i*)), generating a methanol synthesis feed gas (83) and process steam streams (45), (46) and (48). Methanol synthesis feed gas (83) may then undergo methanol synthesis (900) (utilizing boiler feed water (39*h*)) to generate a purified methanol product stream (96) and process steam stream (47).

Figure 4:
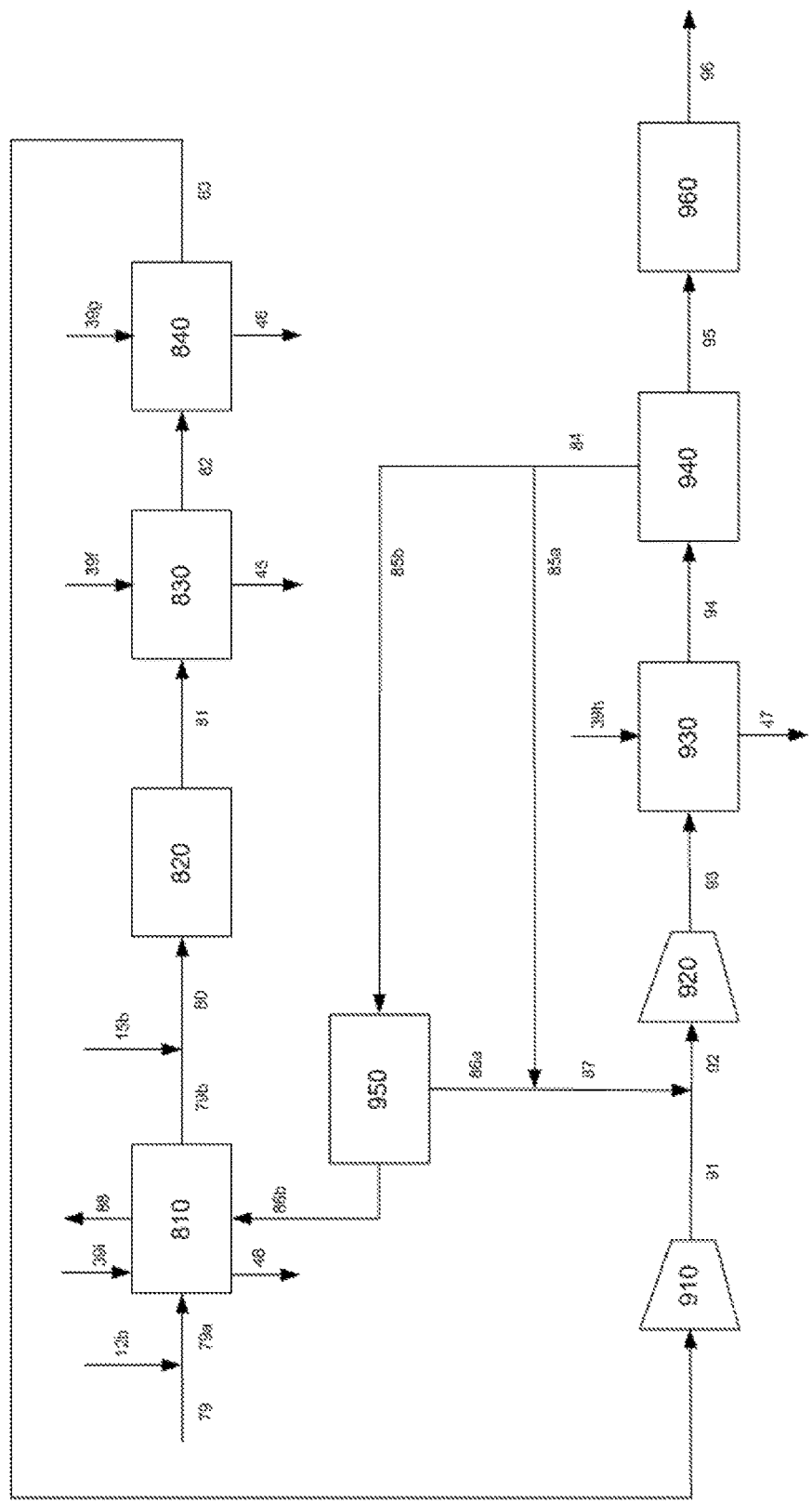
FIG. 4 is a schematic representation of the details of the autothermal reformer and methanol synthesis loop.

FIG. 4 provides more detail on the autothermal reformer (800) and methanol synthesis reactor system (900) treatments discussed above and depicted in FIG. 2.

(e) Steam Generation and Distribution System

The hydromethanation process requires steam at several different pressures. First, steam is needed as a reactant in the hydromethanation reactor (200). Steam is fed to the hydromethanation reactor (200) at a pressure that is higher than the reactor pressure by at least 50 prig (446 kPa). Although the reactor can work with saturated steam, an energy penalty in terms of increased oxygen use, decreased methane production and increased carbon dioxide production must be incurred. As a result, superheated steam at 510° C. (950° F.) at the required pressure is preferred in order to maximize the overall process thermal efficiency. Second, steam is required as a utility to perform various heating duties such as evaporation/crystallization of catalyst solution, reboiler for the AGR and ammonia recovery system, etc.

Referring to FIG. 2, the steam distribution system (11) receives the steam generated by various sources and distributes them to consumers within the process. In particular, process steam streams (45), (46) and (48) are generated by the autothermal reformer (800) and process steam stream (47) is generated by the methanol synthesis reactor system (900) as described above. Process steam streams (40), (41), (42), (45), (46), (47) and (48) are fed to steam distribution system (11).

The main process heat exchanger or boiler (400) following the hydromethanation reactor (200) and the heat exchanger units within the autothermal reformer system (800) and the methanol synthesis loop (900) produce high-pressure steam of the required quality for the hydromethanation reactor (200) and the autothermal reformer system (800). As discussed previously, the temperature of the steam is normally maximized to improve efficiency. The excess high-pressure, saturated or superheated steam is let down in pressure to a level of 50 psig (446 kPa). The saturated steam from the intermediate pressure boiler (410) at 150 psig (1136 kPa) is also let down in pressure to a level of 50 psig (446 kPa). The low-temperature gas cooling system (450) also produces 50 psig steam by recovery of lower grade heat. All sources of 50 psig steam serve as a heat-transfer media for various consumers within the process. Excess 50 psig (446 kPa) steam is let down to 30 psig (304 kPa) and combines with sources of 30 psig (304 kPa) steam within the low temperature gas cooling to be distributed to various consumers within the process. The various steam sources produce sufficient steam at the required levels to meet the requirements of various consumers. As a result, the overall process is steam balanced. Any high-pressure steam in excess of process requirements may be converted to power. The process has a steam demand and a power demand that are met by internal energy integration such that the process requires no net import of steam or power.

Co-Production of Methanol and Substitute Natural Gas

Referring to FIG. 3, the gas processing steps for co-production of methanol and substitute natural gas comprise first cooling the fines-cleaned methane-enriched raw product gas stream (70) in a heat exchanger system (400) against boiler feed water (39*a*) to form high-pressure steam stream (40) and cooled stream (71), further cooling stream (71) against boiler feed water (39*b*) in intermediate-pressure heat exchanger or boiler (410) to generate intermediate-pressure saturated steam (41) and cooled stream (72), scrubbing cooled stream (72) in a hot gas scrubber (420) to form particle-depleted cooled gas (73). High-pressure steam stream (40) and intermediate-pressure saturated steam stream (41) are sent to the steam distribution system (11). These cooling and scrubbing processes were described in more detail above for FIG. 2.

The co-production of methanol and substitute natural gas then continues with the water-gas shift system (500), low temperature gas cooling (450), ammonia recovery (600), acid gas removal (700), cryogenic separation of hydrogen and carbon monoxide from methane (850), and methanol synthesis (900).

(a) Water-Gas Shift (500)

Continuing to refer to FIG. 3, for the co-production of methanol and substitute natural gas the module number of the particle-depleted cooled gas stream (73) may need to be adjusted to the optimum level required by the methanol synthesis loop (900) using water-gas shift system (500). Since the hydromethanation catalyst (31) (see description above for FIG. 1) promotes the water-gas shift reaction, the particle-depleted cooled gas stream (73) has a high molar ratio of hydrogen to carbon monoxide (at least 1.5). Hence, only one shift reactor would be needed as compared to noncatalytic gasification technologies where multiple shift reactors would be required.

When the module number of the methanol synthesis feed gas (83) prepared using the co-production method (i.e., exiting the cryogenic separator (850) (see below)) will be less than 1.75, the particle-depleted cooled gas stream (73) exiting the hot gas scrubber (420) will be split into two portions, a shift inlet stream (73*a*) and a shift bypass stream (73*b*). Shift inlet stream (73*a*) is sent to the water-gas shift system (500) where it is reheated to 450 to 550° F. (232 to 288° C.) and then passed over a sour-shift catalyst (typically cobalt-molybdenum) in a fixed bed reactor to convert a portion of the carbon monoxide and steam to hydrogen and carbon dioxide, forming an effluent gas, shift outlet stream (73*c*). Since the shift reaction is exothermic, the shift outlet stream (73*c*) from the water-gas shift system (500) exchanges heat with shift inlet stream (73*a*) to recover energy. Shift bypass stream (73*b*) bypasses water-gas shift system (500) and is combined with shift outlet stream (73*c*) to form hydrogen-enriched raw product gas stream (73*d*). The fraction of particle-depleted cooled gas (73) that is shifted, i.e., shift inlet stream (73*a*), is controlled to maintain a module number of 1.75 to 2 in the hydrogen-enriched raw product gas stream (73*d*). That is, the shift reaction is carried out only when the module number of the methanol synthesis feed gas produced in part E is less than 1.75. In some cases, the proportion of the particle-depleted cooled gas (73) that is introduced into the water-gas shift reactor (500) to be shifted, i.e., the shift inlet stream (73*a*), may be adjusted and controlled to maintain the module number of 1.75 to 2 in the methanol synthesis feed gas (83).

Methods and reactors for performing the water gas shift reaction on a CO-containing gas stream are well known to those of skill in the art. An example of a suitable shift reactor is illustrated in previously incorporated U.S. Pat. No. 7,074, 373, although other designs known to those of skill in the art are also effective.

(b) Low-Temperature Gas Cooling (450)

Continuing to refer to FIG. 3, the particle-depleted cooled gas (73), or the hydrogen-enriched raw product gas stream (73*d*), if present, next enters the low-temperature gas cooling system (450) and is cooled in a series of heat exchangers within low-temperature gas cooling system (450) to further reduce the temperature to 120° F. (49° C.) to produce a dry raw gas, cooled effluent stream (74). The low-temperature gas cooling system (450) will typically comprise first and second knock-out drums, an air cooler, and a trim cooler.

The particle-depleted cooled gas (73), or the hydrogen-enriched raw product gas stream (73*d*), if present, initially at about 475° F. (246° C.), is first cooled against boiler feed water (39*c*) to generate medium-pressure steam (42) at 50 psig (446 kPa) and low-pressure steam (not shown) at two levels: 30 psig (308 kPa) and 15 psig (205 kPa). Recovery of low-grade heat allows heat integration with other parts of the process where steam at these pressure levels is needed. Medium-pressure steam stream (42) is sent to the steam distribution system (11). As the gas (73), or the gas (73*d*), if present, is cooled down to 200° F. (93° C.), it begins to approach the water dew-point and the condensing water is recovered in a first knock-out drum (not shown). Further cooling of cooled effluent (74) takes place against the air cooler (not shown), which uses ambient air as a cooling medium, and finally the trim cooler (not shown), to achieve a final temperature of 120° F. (49° C.) using cooling water. Ambient conditions at the location of the low-temperature gas cooling system (450) will dictate the amount of air cooling and trim cooling that can be achieved. The stream leaving the trim cooler is sent to the second knock-out drum (not shown) to separate the remaining water from the hydrogen-enriched raw product gas stream (74). The combined condensate from the knock-out drums (not shown) is sent to the ammonia recovery system (600) as described for FIG. 2 above. Cooled effluent (74) exits the low-temperature gas cooling system (450).

(c) Ammonia Recovery System (600) and Acid Gas Removal System (700)

Continuing to refer to FIG. 3 for the co-production of methanol and substitute natural gas, cooled effluent (74) is treated in an ammonia recovery system (600) to form an ammonia-depleted effluent (76) which is subsequently fed to an acid gas removal (AGR) unit (700) to remove a substantial portion of $CO_2$ (77) and a substantial portion of the $H_2S$ (78) and generate a sweetened gas stream (79) as was described above for FIG. 2.

(d) Cryogenic Separation Unit (850)

A cryogenic separation unit (850) is then employed to separate hydrogen and carbon monoxide from methane in the sweetened gas stream (79). The syngas product comprised of hydrogen and carbon monoxide is the methanol synthesis feed gas (83) with a module number that has been optimized for the methanol synthesis loop (900) through the use of the water gas shift system (500). The methane product (98) can be used directly as substitute natural gas and may be liquefied further to produce liquefied natural gas.

The sweetened gas stream (79) from the acid gas removal unit (700) is first cooled against exiting product streams in a multi-pass heat exchanger. The cooled gas, which is close to its dew point, is subject to cryogenic distillation that separates the hydrogen and carbon monoxide from the methane to form the methanol synthesis feed gas (83) and the methane product (98). An important feature of the cryogenic separation process is the ability to generate all the required refrigeration internally. As a result, no external refrigeration cycle is needed to accomplish the separation.

(e) Methanol Synthesis (900) Treatment

The methanol synthesis feed gas (83) may then undergo methanol synthesis (900) (utilizing boiler feed water (39*h*)) to generate a product purified methanol stream (96) and process steam stream (47).

See FIG. 4 for more detail on methanol synthesis reactor system (900) treatment discussed above and depicted in FIG. 3.

(f) Steam Generation and Distribution System

The hydromethanation process requires steam at several different pressures. First, steam is needed as a reactant in the hydromethanation reactor (200). Steam is fed to the hydromethanation reactor (200) at a pressure that is higher than the reactor pressure by at least 50 prig (446 kPa). Although the reactor can work with saturated steam, an energy penalty in terms of increased oxygen use, decreased methane production and increased carbon dioxide production must be incurred. As a result, superheated steam at 510° C. (950° F.) at the required pressure is preferred in order to maximize the overall process thermal efficiency. Second, steam is required as a utility to perform various heating duties such as evaporation/crystallization of catalyst solution, reboiler for the AGR and ammonia recovery system, etc.

Referring to FIG. 3, the steam distribution system (11) receives the steam generated by various sources and distributes them to consumers within the process. In particular, process steam streams (40), (41) and (42) are generated by the heat exchanger system (400), the intermediate-pressure heat exchanger (410) and the low temperature gas cooling unit (450), respectively, and process steam stream (47) is generated by the methanol synthesis reactor system (900). Process steam streams (40), (41), (42), and (47) are fed to steam distribution system (11).

The main process heat exchanger or boiler (400) following the hydromethanation reactor (200) and the heat exchanger units within the methanol synthesis loop (900) produce high-pressure steam of the required quality for the hydromethanation reactor (200). As discussed previously, the temperature of the steam is normally maximized to improve efficiency. The excess high-pressure, saturated or superheated steam is let down in pressure to a level of 50 psig (446 kPa). The saturated steam from the intermediate pressure boiler (410) at 150 psig (1136 kPa) is also let down in pressure to a level of 50 psig (446 kPa). The low-temperature gas cooling system (450) also produces 50 psig steam by recovery of lower grade heat. All sources of 50 psig steam serve as a heat-transfer media for various consumers within the process. Excess 50 psig (446 kPa) steam is let down to 30 psig (304 kPa) and combines with sources of 30 psig (304 kPa) steam within the low temperature gas cooling to be distributed to various consumers within the process. The various steam sources produce sufficient steam at the required levels to meet the requirements of various consumers. As a result, the overall process is steam balanced. Any high-pressure steam in excess of process requirements may be converted to power. The process has a steam demand and a power demand that are met by internal energy integration such that the process requires no net import of steam or power.

Water Treatment and Recovery

For any of the processes described herein, residual contaminants in waste water resulting from any one or more of the trace contaminant removal, sour shift, ammonia removal, acid gas removal and/or catalyst recovery processes can be removed in a waste water treatment unit to allow recycling of the recovered water within the plant and/or disposal of the water from the plant process according to any methods known to those skilled in the art. Depending on the feedstock and reaction conditions, such residual contaminants can comprise, for example, aromatics, CO, $CO_2$, $H_2S$, COS, HCN, $NH_3$, and Hg. For example, $H_2S$ and HCN can be removed by acidification of the waste water to a pH of about 3, treating the acidic waste water with an inert gas in a stripping column, and increasing the pH to about 10 and treating the waste water a second time with an inert gas to remove ammonia (see U.S. Pat. No. 5,236,557). $H_2S$ can be removed by treating the waste water with an oxidant in the presence of residual coke particles to convert the $H_2S$ to insoluble sulfates which may be removed by flotation or filtration (see U.S. Pat. No. 4,478,425). Aromatics can be removed by contacting the waste water with a carbonaceous char optionally containing mono- and divalent basic inorganic compounds (e.g., the solid char product or the depleted char after catalyst recovery, supra) and adjusting the pH (see U.S. Pat. No. 4,113,615). Trace amounts of aromatics ($C_6H_6$, $C_7H_8$, $C_{10}H_8$) can also be removed by extraction with an organic solvent followed by treatment of the waste water in a stripping column (see U.S. Pat. Nos. 3,972,693, 4,025,423 and 4,162,902).

Autothermal Reformer System (800)

Referring to FIG. 4, the sweetened gas stream (79) has a typical composition of 35-40 mol % $H_2$, 19-23 mol % CO and 31-36 mol % $CH_4$, which is unique to the catalytic gasification of hydrocarbonaceous feedstocks carried out in the hydromethanation reactor (200) developed by Great-Point Energy. Stream (79) is mixed with superheated steam (12b) (provided by a steam source such as steam distribution system (11); see FIG. 1) to produce mixed raw gas-steam stream (79a). Stream (79a) is preheated to 538° C. (1000° F.) in a fired heater (810) using heat generated by combustion in air of a fuel source, a hydrogen-depleted pressure swing absorption tail gas stream (86b), to produce flue gas (88) and product stream (79b). After meeting the preheat requirements of stream (79a), the residual heat serves to generate high-pressure, superheated steam (48) at the same conditions as that of heat exchanger system (400) using boiler feed water stream (39i). Oxygen stream (15b), which has been preheated to 204° C. (400° F.), and the product stream (79b) produced from fired heater (810) are combined to form mixed gas-steam stream (80) and fed to an autothermal reformer unit (820). The flow rate of oxygen (15b) and steam (12b) are adjusted to ensure that no carbon deposition takes place within unit (820). The autothermal reformer unit product, effluent gas stream (81), has a dry methane content of less than 2% and a module number R in the range 1.7 to 1.8. The temperature of stream (81) leaving the autothermal reformer is 954° C. (1750° F.). Stream (81) is cooled in the autothermal reformer high-temperature gas-cooling system (830) to 204° C. (400° F.). Boiler feed water (39f) fed to cooling system (830) is converted to high-pressure, superheated steam (45) at 510° C. (950° F.) and 5171 kPa (750 psig). Cooling system (830) is comprised of a steam generation system and a scrubber for final cooling of the gas to 204° C. (400° F.). The cooled effluent stream (82) leaving cooling system (830) is further cooled against boiler feed water stream (39g) and ambient air in autothermal reformer low-temperature gas-cooling system (840) to generate medium pressure steam (46) and a dry, sulfur-free, methane-depleted gas product, methanol synthesis feed gas (83), having a temperature of about 49° C. (120° F.). Methanol synthesis feed gas (83) comprises hydrogen, carbon monoxide and carbon dioxide, may have a module number in the range of 1.75 to 2, and meets the specifications for being processed in the methanol synthesis loop (900).

Methanol Synthesis Loop (900)

Continuing to refer to FIG. 4, the methanol synthesis feed gas stream (83), typically at a pressure of 2068 to 4826 kPa (300 to 700 psig), is compressed to the pressure of the methanol synthesis loop, at least 5000 kPa (1000 to 1150 psig), preferably 7000 to 8000 kPa (1000 to 1150 psig), in a two-stage compression system (910+920). The product gas (91) from the first stage of compression (910) is mixed with a hydrogen-enriched recycle synthesis gas (87) to form gas mixture (92), which is then further compressed to the required final pressure in the second stage of compression (920) to produce a product gas (93). The product gas (91) will have a pressure greater than 5000 kPa (1015 psig), preferably 7000 kPa (1146 psig). The product gas (93) is fed to a methanol synthesis reactor (930) operating under near isothermal conditions. The exothermic heat of reaction is recovered as high-pressure saturated steam (47) at 4238 kPa (600 prig) from boiler feed water stream (39h). The product gas (94) from the methanol synthesis reactor (930) is further cooled in gas cooling unit (940) by first preheating product gas stream (94) to the required inlet conditions and subsequently by exchanging heat in a combination of air coolers and cooling water exchangers. The liquid condensate stream (95) from cooling unit (940) is further processed in a methanol purification unit (960) to separate the product methanol stream (97) from water, higher alcohols and other by-products formed in reactor (930), producing purified methanol (96). The gaseous product from cooling unit (940) is recycle synthesis gas (84), which will comprise at least 50% hydrogen. A portion of stream (84) is taken as purge gas stream (85b) to avoid the build-up of inerts such as methane to high levels in the synthesis loop. Since the purge gas stream (85b) is at high pressure and has a high concentration of hydrogen, it is fed to a pressure swing adsorption unit (950) where hydrogen stream (86a) is recovered at nearly the same pressure as purge gas stream (85b). Hydrogen stream (86a) is recycled to the methanol synthesis loop after combining it with the remaining portion (85a) of the recycle synthesis gas stream (84) to form the hydrogen-enriched recycle synthesis gas (87). The hydrogen-depleted pressure swing absorption tail gas stream (86b) from unit (950) serves as a fuel source for the fired heater unit (810) to preheat mixed raw gas-steam stream (79a) (as was described above in the description of the Autothermal Reformer Unit (800)).

Alternative Products

The methanol synthesis feed gas (83) produced using the autothermal reformer system (800) or the cryogenic separation system (850) has a hydrogen to carbon monoxide molar ratio in the range 1.75 to 2.0. as a result, stream (83) is suitable for producing alternative products that require a hydrogen to carbon monoxide ratio in this range. One such alternative product is dimethyl ether.

One route for dimethyl ether synthesis involves the catalytic reaction of carbon monoxide with hydrogen to form dimethyl ether:

Another process for dimethyl ether production is via catalytic dehydration of methanol:

The benefits of catalytic gasification applied to alternative processes will be similar to that for methanol since they depend on a methanol synthesis feed gas with a hydrogen to carbon monoxide ratio of about 2.

While a number of example embodiments have been provided, the various aspects and embodiments disclosed herein are for purposes of illustration and are not intended to be limiting. Other embodiments can be used, and other changes can be made, without departing from the spirit and scope of the subject matter presented herein. It will be readily understood that the aspects of the disclosure, as generally described herein, and illustrated in the figures, can be arranged, substituted, combined, separated, and designed in a wide variety of different configurations, all of which are explicitly contemplated herein.

We claim:

1. A process for generating a methanol synthesis feed gas from a non-gaseous carbonaceous material and a hydromethanation catalyst, the process comprising the steps of:
   a) preparing a carbonaceous feedstock from the non-gaseous carbonaceous material;
   b) introducing the carbonaceous feedstock, a hydromethanation catalyst, high-pressure, superheated steam, oxygen into a hydromethanation reactor;
   c) reacting the carbonaceous feedstock in the hydromethanation reactor at an operating temperature from about 800° F. (about 427° C.) up to about 1500° F. (about 816° C.), and an operating pressure of at least about 250 psig (about 1825 kPa), to produce a by-product char, and a methane-enriched raw product gas comprising methane, carbon monoxide, hydrogen, carbon dioxide, hydrogen sulfide, steam, ammonia, heat energy and entrained fines;
   d) withdrawing a stream of the by-product char from the hydromethanation reactor as the by-product char stream, wherein the by-product char stream comprises a carbon content and entrained hydromethanation catalyst;
   e) (1) removing a substantial portion of the entrained fines from the methane-enriched raw product gas to form a recovered primary fines stream and a fines-depleted methane-enriched raw product gas stream comprising methane, carbon monoxide, carbon dioxide, hydrogen, hydrogen sulfide, steam, ammonia, heat energy, and residual entrained fines and (2) removing residual entrained fines from the fines-depleted methane-enriched raw product gas stream to form a recovered secondary fines stream and a fines-cleaned methane-enriched raw product gas;
   f) cooling the fines-cleaned methane-enriched raw product gas to generate steam and a cooled stream;
   g) removing additional particulates from the cooled stream to generate a particle-depleted cooled gas;
   h) generating the methanol synthesis feed gas having a module number of 1.75 to 2 by:
      (i) using autothermal reforming by the steps of:
         A) further cooling the particle-depleted cooled gas to generate steam, then recovering the ammonia present in the cooled effluent in an ammonia recovery system to generate an ammonia-depleted effluent;
         B) removing a substantial portion of the carbon dioxide and a substantial portion of the hydrogen sulfide from the ammonia-depleted effluent in an acid gas removal unit to produce a sweetened gas, wherein the sweetened gas comprises hydrogen, carbon monoxide and methane, and has greater than 25% methane on a dry, $CO_2$-free basis;
         C) mixing the sweetened gas with high-pressure, superheated steam and heating the mixture to produce a product stream;
         D) mixing the product stream with oxygen and feeding the mixture into an autothermal reformer unit to form an effluent gas; and
         E) cooling the effluent gas to generate steam and a methanol synthesis feed gas, wherein the methanol synthesis feed gas comprises hydrogen, carbon monoxide and carbon dioxide;
      or
      (ii) using cryogenic separation and co-producing substitute natural gas by the steps of:
         A) forming a hydrogen-enriched raw product gas by
            I) introducing a portion of the particle-depleted cooled gas into a water-gas shift reactor and steam shifting at least a portion of the carbon monoxide to generate an effluent gas; and
            II) combining the remaining portion of the particle-depleted cooled gas with the effluent gas generated by steam shifting to form hydrogen-enriched raw product gas;
            with the proviso that part A is carried out only when the module number of the methanol synthesis feed gas produced in part E is less than 1.75;
         B) cooling the particle-depleted cooled gas, or the hydrogen-enriched raw product gas, if present, to generate steam and a cooled effluent;
         C) recovering the ammonia present in the cooled effluent in an ammonia recovery system to generate an ammonia-depleted effluent;
         D) removing a substantial portion of the carbon dioxide and a substantial portion of the hydrogen sulfide from the ammonia-depleted effluent in acid gas removal unit to produce a sweetened gas; and
         E) feeding the sweetened gas into a cryogenic separator and separating the gas into a substitute natural gas stream and a methanol synthesis feed gas.

2. The process of claim 1, further comprising generating methanol from the methanol synthesis feed gas.

3. The process of claim 2, wherein the process has a steam demand and a power demand that are met by internal energy integration such that the process requires no net import of steam or power.

4. The process of claim 3, wherein the hydromethanation catalyst comprises an alkali metal.

5. The process of claim 4, wherein the alkali metal is potassium.

6. The process of claim 4, further comprising treating all or a portion of the by-product char stream in a catalyst recovery unit comprising a quench tank and a quench medium, the treatment comprising the steps of:
   a) quenching the by-product char stream with the quench medium to extract a portion of the entrained catalyst to generate a carbon- and catalyst-depleted char and liberated hydromethanation catalyst;
   b) withdrawing a stream of carbon- and catalyst-depleted char from the catalyst recovery unit as the carbon- and catalyst-depleted char stream; and
   c) withdrawing a stream of liberated hydromethanation catalyst from the catalyst recovery unit as the recovered hydromethanation catalyst stream.

7. The process of claim 6, further comprising the step of feeding at least a portion of the recovered secondary fines stream to the catalyst recovery unit.

8. The process of claim 7, wherein the hydromethanation catalyst comprises at least a portion of the recovered hydromethanation catalyst stream.

9. The process of claim 2, wherein the methanol synthesis feed gas is generated by the autothermal reforming process of claim 1, step h, part (i).

10. The process of claim 9, wherein the product stream produced in step h, part (i) C, has a temperature of at least 1000° F. (538° C.).

11. The process of claim 2, wherein the methanol synthesis feed gas is generated by the cryogenic separation and co-production process of claim 1, step h, part (ii).

12. The process of claim 1, further comprising the step of converting the methanol synthesis feed gas to dimethyl ether.

13. The process of claim 2, further comprising the step of converting the methanol to dimethyl ether.

* * * * *